US009567392B2

(12) United States Patent
Simon et al.

(10) Patent No.: US 9,567,392 B2
(45) Date of Patent: Feb. 14, 2017

(54) JCV NEUTRALIZING ANTIBODIES

(71) Applicant: Biogen MA Inc., Cambridge, MA (US)

(72) Inventors: Kenneth Simon, Cambridge, MA (US); Thomas Cameron, Cambridge, MA (US); Deping Wang, Sharon, MA (US); Joseph Arndt, Peabody, MA (US); Mia Rushe, Everett, MA (US); Justin Caravella, Cambridge, MA (US); Eric Day, Palo Alto, CA (US)

(73) Assignee: Biogen MA Inc., Cambridge, MA (US)

(*) Notice: Subject to any disclaimer, the term of this patent is extended or adjusted under 35 U.S.C. 154(b) by 0 days.

(21) Appl. No.: 14/386,262

(22) PCT Filed: Mar. 15, 2013

(86) PCT No.: PCT/US2013/031842
§ 371 (c)(1),
(2) Date: Sep. 18, 2014

(87) PCT Pub. No.: WO2013/142299
PCT Pub. Date: Sep. 26, 2013

(65) Prior Publication Data

US 2015/0050271 A1 Feb. 19, 2015

Related U.S. Application Data

(60) Provisional application No. 61/613,214, filed on Mar. 20, 2012.

(51) Int. Cl.
*C07K 16/08* (2006.01)

(52) U.S. Cl.
CPC ......... *C07K 16/084* (2013.01); *C07K 2317/24* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2007/0280941 | A1 | 12/2007 | Chung et al. |
| 2009/0148447 | A1 | 6/2009 | Ledbetter et al. |
| 2009/0280128 | A1 | 11/2009 | Kamogawa et al. |
| 2010/0028336 | A1 | 2/2010 | Ebel et al. |
| 2010/0129437 | A1 | 5/2010 | Gaillard |
| 2011/0219478 | A1 | 9/2011 | Kav et al. |
| 2015/0056188 | A1 | 2/2015 | Simon et al. |

FOREIGN PATENT DOCUMENTS

| | | | |
|---|---|---|---|
| EP | 13765090.9 | | 6/2015 |
| EP | 13763643.7 | | 2/2016 |
| WO | WO 2009/155723 | A2 | 12/2009 |
| WO | WO 2010/090757 | A1 | 8/2010 |
| WO | WO 2010/129959 | A1 | 11/2010 |
| WO | WO 2011/050384 | A2 | 5/2011 |

OTHER PUBLICATIONS

Suzuki et al. Broad Distribution of the JC Virus Receptor Contrasts with a Marked Cellular Restriction of Virus Replication. Virology 286: 100-112 (2001).*
Pastrana et al. Characterization of monoclonal antibodies specific for the Merkel cell polyomavirus capsid. Virology 405: 20-25 (2005).*
Randhawa et al. Identification of species-specific and cross-reactive epitopes in human polyomavirus capsids using monoclonal antibodies. J Gen Virol. Mar. 2009;90(Pt 3):634-9.*
Murata et al. Identification of a neutralization epitope in the VP1 capsid protein of SV40.Virology. Nov. 10, 2008;381(1):116-22. Epub Sep. 11, 2008.*
Chames et al. Therapeutic antibodies: successes, limitations and hopes for the future. British Journal of Pharmacology (2009), 157, 220-233.*
Spieker-Polet et al. Rabbit monoclonal antibodies: generating a fusion partner to produce rabbit-rabbit hybridomas. Proc Natl Acad Sci U S A. Sep. 26, 1995; 92(20): 9348-9352.*

Gee et al., Modeling a sialic acid binding pocket in the external loops of JC virus VP1. J Biol Chem. Nov. 19, 2004;279(47):49172-6. Epub Sep. 3, 2004.

Henmi et al., Establishment of an immunoscreening system using recombinant VP1 protein for the isolation of a monoclonal antibody that blocks JC virus infection. Biochem Biophys Res Commun. Feb. 4, 2005;327(1):242-51.

Suzuki et al., Broad distribution of the JC virus receptor contrasts with a marked cellular restriction of virus replication. Virology. Jul. 20, 2001;286(1):100-12.

Youssef et al., Anti-JCV neutralizing antibodies as a potential therapy for the treatment of PML. J Neurovirol. May 2012;18: S125.

* cited by examiner

*Primary Examiner* — Nick Zou

(74) *Attorney, Agent, or Firm* — Wolf, Greenfield & Sacks, P.C.

(57) ABSTRACT

In one aspect, the disclosure provides neutralizing antibodies against JCV and methods for the treatment of PML. In some embodiments, aspects of the invention relate to an isolated JC-vims neutralizing monoclonal antibody against JCV capsid protein VPI (JCV-VP1). In some embodiments, the antibody suppresses infectivity of the JC-vims. In some embodiments, the antibody binds the sialic acid binding pocket of JCV-VP1.

12 Claims, 20 Drawing Sheets

Calculation of EC50, EC80, and EC90 Values

| HA3220 1.75 d | Anti-JCV EC50 | EC80 | EC90 | Anti-BKV EC50 | EC80 | EC90 |
|---|---|---|---|---|---|---|
| R-mAb 399 | 4.5 | 15.8 | 25.0 | nc | nc | nc |
| R-mAb 322 | 185.8 | 2293.0 | 5710.0 | 0.1 | 0.7 | 0.3 |
| R-mAb 117-11 | 21.6 | 46.9 | 66.8 | 77.7 | 151.3 | 392.2 |
| R-mAb 117-10 | 8.3 | 34.7 | 57.2 | 12.6 | 26.9 | 48.3 |
| R-mAb 117-7 | 11.2 | 32.5 | 57.9 | 13.4 | 40.5 | 63.3 |

| HA3220 7.7 d | Anti-JCV EC50 | EC80 | EC90 | Anti-BKV EC50 | EC80 | EC90 |
|---|---|---|---|---|---|---|
| R-mAb 399 | 4.3 | 15.3 | 29.0 | nc | nc | nc |
| R-mAb 322 | 162.3 | 9063.0 | 31320.0 | nc | ambiguous | nc |
| R-mAb 117-11 | 20.0 | 50.5 | 75.8 | 41.9 | 122.4 | 244.6 |
| R-mAb 117-10 | 10.0 | 29.5 | 46.6 | 14.4 | 37.6 | 111.6 |
| R-mAb 117-7 | 9.0 | 31.5 | 59.1 | 7.9 | 70.2 | 106.1 |

| HA3839 6.5 d | Anti-JCV EC50 | EC80 | EC90 | Anti-BKV EC50 | EC80 | EC90 |
|---|---|---|---|---|---|---|
| R-mAb 399 | 4.9 | 15.9 | 28.0 | nc | 0.1 | nc |
| R-mAb 322 | 193.7 | 5851.0 | 17510.0 | interrupted | 0.0 | ambiguous |
| R-mAb 117-11 | 22.5 | 51.1 | 82.5 | 21.0 | 81.3 | 128.2 |
| R-mAb 117-10 | 10.0 | 31.3 | 51.4 | 7.9 | 67.4 | 178.6 |
| R-mAb 117-7 | 10.7 | 41.6 | 86.7 | 9.2 | 102.2 | 199.1 |

| HRPTEpiC5037 4.2 d | Anti-JCV EC50 | EC80 | EC90 | Anti-BKV EC50 | EC80 | EC90 |
|---|---|---|---|---|---|---|
| R-mAb 399 | | | | nc | nc | nc |
| R-mAb 322 | | | | ambiguous | ambiguous | ambiguous |
| R-mAb 117-11 | | | | 34.8 | 40.7 | 43.6 |
| R-mAb 117-10 | | | | 18.0 | 29.9 | 37.6 |
| R-mAb 117-7 | | | | 15.7 | 22.7 | 29.1 |

Values given as ng/ml

Fig. 3

| Temperature 25.8 471-WT | 1 | 2 | 3 | 4 | 5 | 6 | 7 | 8 | 9 | 10 | 11 | 12 |
|---|---|---|---|---|---|---|---|---|---|---|---|---|
| | 2.2892 | 2.429 | 1.5819 | 1.6797 | 2.4709 | 2.3032 | 2.2426 | 2.3727 | 1.5185 | 1.6004 | 2.4339 | 2.1823 |
| | 2.4044 | 2.5007 | 1.5064 | 1.6541 | 2.4367 | 2.4273 | 2.291 | 2.4472 | 1.4488 | 1.6178 | 2.3942 | 2.3025 |
| | 2.4428 | 2.4966 | 1.6641 | 1.6534 | 2.4679 | 2.4787 | 2.4244 | 2.4891 | 1.6134 | 1.5778 | 2.4029 | 2.3824 |
| | 2.5554 | 2.5388 | 1.7362 | 1.7066 | 2.422 | 2.5484 | 2.5069 | 2.4848 | 1.6776 | 1.6496 | 2.3734 | 2.3629 |
| | 2.4881 | 0.0752 | 1.5151 | 2.0824 | 2.5729 | 1.7729 | 2.3737 | 0.0764 | 1.4514 | 1.9033 | 2.5371 | 1.5579 |
| | 2.422 | 0.0794 | 1.6759 | 0.1684 | 2.4737 | 1.827 | 2.3517 | 0.0727 | 1.6798 | 0.1563 | 2.4585 | 1.4216 |
| | 2.4336 | 0.0974 | 1.6938 | 0.202 | 2.556 | 2.055 | 2.4232 | 0.0981 | 1.7072 | 0.1898 | 2.5737 | 1.7531 |
| | 2.5564 | 0.1199 | 1.7725 | 0.2836 | 2.5282 | 0.1265 | 2.5348 | 0.1115 | 1.7486 | 0.2702 | 2.4489 | 0.0965 |

7-12 douplicate to 1-6

| Temperature 25.8 55F(485) | 1 | 2 | 3 | 4 | 5 | 6 | 7 | 8 | 9 | 10 | 11 | 12 |
|---|---|---|---|---|---|---|---|---|---|---|---|---|
| | 2.136 | 2.3371 | 1.6006 | 1.6645 | 2.3839 | 2.2497 | 2.0329 | 2.3013 | 1.5227 | 1.6088 | 2.3428 | 2.0036 |
| | 2.2773 | 2.4044 | 1.5522 | 1.6856 | 2.3807 | 2.4274 | 2.1808 | 2.3303 | 1.4484 | 1.6099 | 2.2757 | 2.1863 |
| | 2.2517 | 2.3837 | 1.6366 | 1.5942 | 2.3144 | 2.2751 | 2.0641 | 2.2974 | 1.588 | 1.5276 | 2.2402 | 2.2193 |
| | 2.3629 | 2.3174 | 1.6802 | 1.7124 | 2.2698 | 2.221 | 2.1439 | 2.2058 | 1.5774 | 1.5858 | 2.2449 | 2.2922 |
| | 2.3098 | 0.0889 | 1.5231 | 1.8793 | 2.4926 | 1.7118 | 2.0858 | 0.0635 | 1.4516 | 1.538 | 2.3943 | 1.1469 |
| | 2.2546 | 0.0826 | 1.6325 | 0.1444 | 2.3028 | 1.4469 | 2.0376 | 0.0736 | 1.559 | 0.114 | 2.2889 | 1.0918 |
| | 2.2417 | 0.0871 | 1.5846 | 0.1598 | 2.4264 | 1.8343 | 2.1499 | 0.0802 | 1.6425 | 0.1541 | 2.4023 | 1.4388 |
| | 2.3749 | 0.1056 | 1.6511 | 0.2147 | 2.3852 | 0.0881 | 2.1554 | 0.0954 | 1.6176 | 0.2016 | 2.3258 | 0.0878 |

Fig. 4-1

| Temperature 25.8 269F(502) | 1 | 2 | 3 | 4 | 5 | 6 | 7 | 8 | 9 | 10 | 11 | 12 |
|---|---|---|---|---|---|---|---|---|---|---|---|---|
| | 1.0633 | 1.5141 | 1.3141 | 1.4211 | 1.9558 | 1.5392 | 1.1383 | 1.5109 | 1.2616 | 1.2606 | 1.9404 | 1.4129 |
| | 1.1792 | 1.5824 | 1.2433 | 1.3656 | 1.8309 | 1.8111 | 1.3245 | 1.7244 | 1.201 | 1.2306 | 1.9806 | 1.5174 |
| | 1.2653 | 1.7061 | 1.363 | 1.3637 | 1.7442 | 1.8063 | 1.4132 | 1.872 | 1.2011 | 1.2487 | 1.7526 | 1.7526 |
| | 1.3786 | 1.2438 | 1.378 | 1.3891 | 1.5538 | 1.7777 | 1.6565 | 1.4758 | 1.3187 | 1.2776 | 1.7974 | 1.4563 |
| | 1.2213 | 0.1124 | 1.1777 | 2.0515 | 2.067 | 1.7608 | 1.3167 | 0.0949 | 1.0533 | 1.6367 | 2.0339 | 1.4199 |
| | 1.0035 | 0.1024 | 1.3097 | 0.1788 | 1.5748 | 1.7445 | 1.1634 | 0.0938 | 1.1773 | 0.1683 | 1.7627 | 1.2401 |
| | 1.0627 | 0.1077 | 1.3127 | 0.1954 | 1.9981 | 2.0452 | 1.0775 | 0.097 | 1.3776 | 0.2 | 1.8693 | 1.5139 |
| | 1.3302 | 0.1352 | 1.2434 | 0.2557 | 1.5568 | 0.1207 | 1.1735 | 0.114 | 1.235 | 0.2549 | 1.4768 | 0.1059 |

| Temperature 25.8 271H | 1 | 2 | 3 | 4 | 5 | 6 | 7 | 8 | 9 | 10 | 11 | 12 |
|---|---|---|---|---|---|---|---|---|---|---|---|---|
| | 0.9157 | 1.1761 | 0.1876 | 0.1896 | 1.3498 | 1.0079 | 0.9002 | 1.0636 | 0.1703 | 0.1814 | 1.3466 | 0.9353 |
| | 1.1703 | 1.3751 | 0.1892 | 0.2088 | 1.4823 | 1.4817 | 1.1993 | 1.3674 | 0.183 | 0.211 | 1.4414 | 1.3513 |
| | 1.2471 | 1.5675 | 0.2113 | 0.2017 | 1.5288 | 1.5708 | 1.5014 | 1.654 | 0.2097 | 0.2006 | 1.3642 | 1.3083 |
| | 1.4808 | 1.2911 | 0.2154 | 0.2176 | 1.4563 | 1.5589 | 1.5193 | 1.4537 | 0.2083 | 0.1998 | 1.371 | 1.3059 |
| | 1.2829 | 0.0895 | 0.1922 | 1.0231 | 1.7398 | 0.9234 | 1.3643 | 0.079 | 0.1938 | 1.0019 | 1.6066 | 0.6786 |
| | 1.2248 | 0.0831 | 0.2143 | 0.098 | 1.4979 | 0.7621 | 1.2535 | 0.0799 | 0.212 | 0.1125 | 1.2999 | 0.5857 |
| | 1.2693 | 0.1021 | 0.2275 | 0.1223 | 1.692 | 1.0455 | 1.2723 | 0.0977 | 0.2322 | 0.118 | 1.5952 | 0.8588 |
| | 1.2659 | 0.135 | 0.3267 | 0.1497 | 1.4151 | 0.113 | 1.346 | 0.0922 | 0.3001 | 0.1514 | 1.3289 | 0.0965 |

Fig. 4-2

| Temperature 25.8 60E | 1 | 2 | 3 | 4 | 5 | 6 | 7 | 8 | 9 | 10 | 11 | 12 |
|---|---|---|---|---|---|---|---|---|---|---|---|---|
| | 0.1276 | 0.1377 | 1.2509 | 1.335 | 0.157 | 0.1521 | 0.1436 | 0.1407 | 1.279 | 1.3671 | 0.1614 | 0.1344 |
| | 0.1517 | 0.1478 | 1.2516 | 1.3671 | 0.1742 | 0.1602 | 0.1477 | 0.1582 | 1.211 | 1.3716 | 0.152 | 0.1466 |
| | 0.1589 | 0.1594 | 1.354 | 1.3329 | 0.1716 | 0.1729 | 0.1738 | 0.1821 | 1.3902 | 1.3254 | 0.1544 | 0.1541 |
| | 0.1565 | 0.1358 | 1.4077 | 1.4058 | 0.1601 | 0.1656 | 0.1689 | 0.1494 | 1.3819 | 1.4035 | 0.1833 | 0.1732 |
| | 0.1361 | 0.0721 | 1.2101 | 1.6783 | 0.1919 | 1.4302 | 0.1666 | 0.0717 | 1.2374 | 1.5498 | 0.1631 | 1.3068 |
| | 0.1403 | 0.0784 | 1.3744 | 0.1364 | 0.1684 | 1.3839 | 0.1458 | 0.1014 | 1.4149 | 0.1457 | 0.1523 | 1.2703 |
| | 0.1542 | 0.0816 | 1.4229 | 0.1692 | 0.1917 | 1.7859 | 0.1736 | 0.0915 | 1.4511 | 0.1833 | 0.1887 | 1.5773 |
| | 0.1881 | 0.1247 | 1.2828 | 0.2267 | 0.192 | 0.1052 | 0.1706 | 0.1046 | 1.2778 | 0.233 | 0.1739 | 0.1014 |

| Temperature 25.8 66H | 1 | 2 | 3 | 4 | 5 | 6 | 7 | 8 | 9 | 10 | 11 | 12 |
|---|---|---|---|---|---|---|---|---|---|---|---|---|
| | 1.7012 | 1.8744 | 0.5707 | 0.593 | 2.0382 | 1.7535 | 1.653 | 1.9112 | 0.5351 | 0.5695 | 2.0589 | 1.7929 |
| | 1.8596 | 1.9894 | 0.5027 | 0.5599 | 2.0283 | 2.0751 | 1.7914 | 1.9836 | 0.4398 | 0.5112 | 2.0652 | 2.0415 |
| | 1.7923 | 2.055 | 0.5332 | 0.5391 | 2.0644 | 2.1011 | 1.9913 | 2.1002 | 0.4795 | 0.4981 | 2.0094 | 2.0652 |
| | 2.0046 | 1.8756 | 0.5679 | 0.558 | 1.9793 | 2.1373 | 2.1105 | 1.9221 | 0.5052 | 0.497 | 1.9492 | 2.0342 |
| | 1.8329 | 0.0766 | 0.493 | 1.2099 | 2.2414 | 0.9386 | 2.0464 | 0.0664 | 0.4816 | 0.9487 | 2.101 | 0.9172 |
| | 1.8452 | 0.0658 | 0.5734 | 0.082 | 2.058 | 0.9264 | 1.957 | 0.0757 | 0.5798 | 0.1013 | 2.033 | 0.8083 |
| | 1.8111 | 0.0915 | 0.6177 | 0.1056 | 2.3343 | 1.3325 | 2.0215 | 0.0971 | 0.6499 | 0.1054 | 2.213 | 1.146 |
| | 1.9717 | 0.1115 | 0.7052 | 0.1228 | 2.022 | 0.1283 | 1.9925 | 0.1102 | 0.7162 | 0.1286 | 2.066 | 0.1093 |

Fig. 4-3

Clones

| 411-1 | 411-6 | 497-1 | 497-9  | 399-1 | 399-9  |
| 411-2 | 411-7 | 497-2 | 497-10 | 399-2 | 399-10 |
| 411-3 | 411-8 | 497-3 | 497-11 | 399-3 | 399-11 |
| 411-4 | 411-9 | 497-4 | 497-12 | 399-4 | 399-12 |
| 411-5 | buffer | 497-5 | 417-5 | 399-5 | 417-1 |
| 411-6 | buffer | 497-6 | 422-1 | 399-6 | 417-2 |
| 411-7 | buffer | 497-7 | 422-2 | 399-7 | 417-3 |
| 411-8 | buffer | 497-8 | 422-3 | 399-8 | 417-4 | duoblicate

| clones | color | 471-WT | L55F | S269F | Q271H | K60E | D66H |
|---|---|---|---|---|---|---|---|
| 411 | Red | ++++ | ++++ | ++ | ++ | - | +++ |
| 497 | Blue | +++ | +++ | ++ | - | ++ | + |
| 417 | Purple | +++ | +++ | +++ | ++ | ++ | ++ |
| 399 | Black | ++++ | ++++ | +++ | +++ | - | +++ |
| 422 | Brown | - | - | - | - | - | - |

Binding activity

Fig. 4-4

Candidate Affinity ELISA

| | CH-399 | BIIB048 | $H0_{V50A}L2_{N31A}$ | $H0_{V50A}L2_{N31G}$ |
|---|---|---|---|---|
| Mad-1 | ≤0.1 | ≤0.1 | ≤0.1 | ≤0.1 |
| Type 3 | ≤0.1 | ≤0.1 | ≤0.1 | ≤0.1 |
| Type 1B | ≤0.1 | ≤0.1 | ≤0.1 | ≤0.1 |
| Type 2A | ≤0.1 | ≤0.1 | ≤0.1 | ≤0.1 |
| 269F-type 3 | 2.8 | nb | 0.17 | ≤0.1 |
| 269Y-type 3 | 4 | nb | 3.7 | ≤0.1 |
| 269F-type 1B | >66 | nb | 3.7 | ≤0.1 |
| S267F | ≤0.1 | ≤0.1 | ≤0.1 | ≤0.1 |
| N265D | ≤0.1 | ≤0.1 | ≤0.1 | ≤0.1 |
| Q271H | ≤0.1 | ≤0.1 | ≤0.1 | ≤0.1 |
| D66H | ≤0.1 | 0.12 | 0.15 | ≤0.1 |
| K60E | >>>66 | nb | nb | nb |
| K60N | >>66 | nb | nb | nb |
| L55F | ≤0.1 | ≤0.1 | ≤0.1 | ≤0.1 |

Fig. 5

Biacore Affinity Data

| $K_D$ (nM) | Type 1B wt | | Type 2A* wt | | MAD-1 wt | | Type 3 wt | | Type 3 S269F | | Type 3 S269Y | | Type 3 L55F | |
|---|---|---|---|---|---|---|---|---|---|---|---|---|---|---|
| | Fab | mAb | Fab | mAb | Fab | mAb | Fab | mAb | Fab | mAb | Fab | mAb | Fab | mAb |
| Chimeric | | | 1.9 | ≤0.01 | 0.4 | ≤0.01 | 0.5 | ≤0.01 | | | | | | |
| H0/L0 | | | 12.6 | | 50 | | 50 | | n.b | n.b | n.b | n.b | | |
| V50A/N31A | | | 21.1 | | 8.9 | 0.9 | | | 41 | 0.04 | 20.7 | 0.57 | | |

| $K_D$ (nM) | Type 3 D66H | | Type 3 Q271H | | Type 3 K60E | | Type 3 N265D | | Type 3 K60N | | Type 3 S269F | | Type1B S269F | |
|---|---|---|---|---|---|---|---|

JCV VP1 Combined Mutation Frequency
52 Genbank, 19 Tysabri, 40 Italian HIV

S269F, 20.7%
L55F, 18.0%
None, 11.7%
Complex, 7.2%
D66H, 4.5%
N265D, 4.5%
S267F, 4.5%
N74S, 3.6%
S123C, 3.6%
S269Y, 3.6%
K60M, 2.7%
K60N, 1.8%
S267L, 1.8%
Q271H, 1.8%
K60E, 0.9%
S61L, 0.9%
D66N, 0.9%
D66G, 0.9%
E69D, 0.9%
H122R, 0.9%
N265T, 0.9%
N265H, 0.9%
S267Y, 0.9%
Q271R, 0.9%
V283I 0.9%

Genbank sequences include non-brain (14) and brain derived (38) samples. L55F (2) and S269F (1) were removed from the "comlex" group and included in their appropriate category

Fig. 7

Virus Preps

- Current purifications:
  - Benzonase/Neuraminidase Tx of CM
  - Spun thru 40% sucrose cushion
  - Resuspended: 0.01x original volume in HBSS++
  - Viruses:
    - 2Awt
    - 2A L55F    •2A N265D
    - 2A S269F   •2A S269Y
    - 2A K60E    •2A K60M
    - 2A S267F   •2A Q271F**
    - 2A D66H  •2A S61P
    - MAD1 (1Av wt)
    - All prep'd from post-infection material except ** were post-transfection
  - All titers (Geq) evaluated by qPCR

Fig. 9

Viral Mutant Infectivity: mAb Blocking Assay

- Design:
  - 293ft cells: 96w format, 15e3 cells/well; Fn coated plates @ t= (-18hr)
  - 12 Viruses
    - 2A scaffold: wt, S269F, L55F, S269Y; K60E; K60M; S267F; N265D; Q271F; D66H; S61P
    - MAD1
    - 1.5e9GEq/well (MOI=1e5)
  - mAbs
    - BIIB48, hu399 50-31G
    - 3-fold serial dilutions: 1000-0.46ng/ml final conc
  - 2 replicates ea condition per plate; 1 virus x 3mAbs per plate
  - Pre-inc virus + mAb 90min RT (low volume, 35ul)
  - Outgrow in presence mAb (@ appropriate conc, fv 100ul)
  - Aspirate media and replace with mAb supplemented media @ 3dpi, 7dpi
  - Harvest @ 11dpi
    - aspirate media, wash PBS-$Ca^{++}$, Lyse in 100ul/well modified RIPA buffer (Y.Gao)
- Initial read-out:
  - Western (portion of 1 replicate ea condition)
    - All samples 7.5ul lysate/well
    - Detect with PAB597 1ug/ml O/N 4*C>> DαM-HRP 1::50K 90min >> detect Pierce SuperSignal West Dura ECL reagent

Fig. 10

**Mutant Virus - mAb Protection Against Infection of 293ft:
2Awt, S269F, S269Y, L55F, K60E, K60M**

Fig. 11

Mutant Virus - mAb Protection Against Infection of 293ft:
S61P, D66H, N265D, S267F, Q271H, MAD1wt

Fig. 12

Mutant Virus - mAb Protection: BIIB048, H0L2 V50A/N31G vs Mutant VP1 Infection of 293ft wt (S269F?)

Mutant Virus - mAb ProtectionAgainst Infection of 293ft:
S61P, D66H, N265D, S267F, Q271H, MAD1wt

Fig. 14

VLP Binding ELISA – Robot version

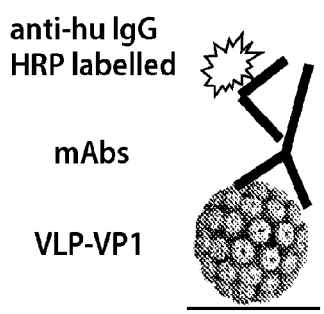

anti-hu IgG
HRP labelled mAbs

VLP-VP1

- Coat overnight at 4°C with 0.2ug/ml VLP diluted in D-PBS, 50 ul/well
- 2 washes with PBST
- Block 1h at RT with casein BB
- 2 washes with PBST
- 1 h reaction with 3fold dilutions, duplicate plates
- 5 washes with PBST
- 1 h reaction with Goat anti-HuIgG Fc specific – F(ab')2 – HRP(Jackson #109-036-098) 1:10 k
- 5 washes with PBST
- 4 minutes TMB color Development
- Stop with 1N H2SO4

Fig. 15

Final ELISA's:
Select 399 Variants on all Available VLP's

- 399 descendants:  ch399

BIIB 048
  5031G
- VLP's (all prepared TFF/TMAE method unless * indicates hybrid UC/TMAE method:

| | | | | | |
|---|---|---|---|---|---|
| WT (1A) | | L55F(1B) | N265D (1B)* | | S269F (1B) |
| WT (1B) | | L55F (3) | N265D (3) | | S269F (3) |
| WT (2A) | | K60E (3) | S267F (1B) | | S269Y (1B)* |
| WT (2B) | | K60N (3) | S267F (3) | | S269Y (3) |
| WT (3) | D66H (1B) | | | Q271H (3) | |
| WT (Mad-1) | D66H (3) | | | | |

- 3-fold dilutions starting at 2 ug/ml (12 points) duplicate plates
- 10 or 20 plates per day; some VLP' s duplicated from day to day to demonstrate reproducibiliy

Fig. 16

ELISA EC$_{50}$, nM

|  | ch399 | BIIB048 | 5031G |
|---|---|---|---|
| WT (1A) | <0.1 | <0.1 | <0.1 |
| WT (1B) | <0.1 | <0.1 | <0.1 |
| WT (2A) | <0.1 | <0.1 | <0.1 |
| WT (2B) | <0.1 | <0.1 | <0.1 |
| WT (3) | <0.1 | <0.1 | <0.1 |
| WT (Mad-1) | <0.1 | <0.1 | <0.1 |
| L55F (1B) | <0.1 | <0.1 | <0.1 |
| L55F (3) | <0.1 | 0.12 | 0.12 |
| K60E (3) | >>10 | nb | nb |
| K60N (3) | >>10 | nb | nb |
| D66H (1B) | 0.1 | 0.11 | 0.17 |
| D66H (3) | 0.13 | 0.19 | 0.14 |
| N265D (1B) | <0.1 | 0.49 | <0.1 |
| N265D (3) | <0.1 | <0.1 | <0.1 |
| S267F (1B) | 0.96 | nb | <0.1 |
| S267F (3) | <0.1 | <0.1 | <0.1 |
| S269F (1B) | >10 | nb | <0.1 |
| S269F (3) | 1.6 | nb | <0.1 |
| S269Y (1B) | >>10 | nb | 1.6 |
| S269Y (3) | 1.5 | nb | <0.1 |
| Q271H (3) | <0.1 | <0.1 | <0.1 |

Fig. 17

JCV NEUTRALIZING ANTIBODIES

RELATED APPLICATIONS

This application is a national stage filing under 35 U.S.C. §371 of international PCT application number PCT/US2013/031842, filed Mar. 15, 2013, which was published under PCT Article 21(2) in English, and claims the benefit under 35 U.S.C. §119 of U.S. provisional application No. 61/613,214, filed Mar. 20, 2012, the entire contents of each of which is incorporated herein by reference.

FIELD OF THE INVENTION

In one aspect, the disclosure relates to antibodies and uses thereof.

BACKGROUND

JC polyomavirus (JCV) is the causative agent of a demyelinating disease of the central nervous system, progressive multifocal leukoencephalopathy (PML). The incidence of PML can be related to a weakened immune system or treatment with immunosuppressants. Currently, there is no specific antiviral therapy that has been proven effective for treatment of PML.

SUMMARY OF THE INVENTION

In some embodiments, aspects of the invention relate to an isolated JC-virus neutralizing monoclonal antibody against JCV capsid protein VP1 (JCV-VP1). In some embodiments, the antibody suppresses infectivity of the JC-virus. In some embodiments, the antibody binds the sialic acid binding pocket of JCV-VP1.

In some embodiments, the antibody binds JCV-VP1 comprising one or more of the following mutations: S269F, S269Y, S267F, N265D, Q271H, D66H, K60E, K60N and L55F.

In some embodiments, the antibody binds JCV-VP1 comprising mutation S269F, JCV-VP1 comprising mutation S269Y, JCV-VP1 comprising mutation S267F, JCV-VP1 comprising mutation N265D, JCV-VP1 comprising mutation Q271H, JCV-VP1 comprising mutation D66H, and JCV-VP1 comprising mutation L55F.

In some embodiments, the JCV-VP1 is from JCV strain type 1a, 1b, 2a, 2b, 3, 4, or 7.

In some embodiments, the antibody comprises one or more of the following CDRs: CDR1: QASQSIGXNLA (SEQ ID NO:18, 399-l N31X), CDR1: GFSFDRNYWIX (SEQ ID NO:33, 399-h C35X), CDR2: LASYLAS (SEQ ID NO:3, 399-l), CDR2: XISAGGSGNTYYATWAKG (SEQ ID NO:37, 399-h C50X), CDR3: QSSYYSPNDNA (SEQ ID NO:4, 399-l), CDR3: FYSGGGYYAGYFTL (SEQ ID NO:9, 399-h), and CDR sequences with up to two amino acid mutations as compared to SEQ ID NOs:18, 33, 3, 37, 4 and 9.

In some embodiments, the antibody comprises one or more of the following CDRs: CDR1: QASQSIGGNLA (SEQ ID NO:17, 399-l N31G), CDR1: GFSFDRNYWIA (SEQ ID NO:31, 399-h C35A), CDR2: LASYLAS (SEQ ID NO:3, 399-l), CDR2: AISAGGSGNTYYATWAKG (SEQ ID NO:35, 399-h C50A), CDR3: QSSYYSPNDNA (SEQ ID NO:4, 399-l), CDR3: FYSGGGYYAGYFTL (SEQ ID NO:9, 399-h), and CDR sequences with up to two amino acid mutations as compared to SEQ ID NOs:17, 31, 3, 35, 4 and 9.

In some embodiments, the antibody comprises one or more of the following CDRs: CDR1: QASQSIGGNLA (SEQ ID NO:17, 399-l N31G), CDR1: GFSFDRNYWIA (SEQ ID NO:31, 399-h C35A), CDR2: LASYLAS (SEQ ID NO:3, 399-l), CDR2: AISAGGSGNTYYATWAKG (SEQ ID NO:35, 399-h C50A), CDR3: QSSYYSPNDNA (SEQ ID NO:4, 399-l), and CDR3: FYSGGGYYAGYFTL (SEQ ID NO:9, 399-h).

In some embodiments, the antibody comprises one or more of the following CDRs: CDR3: QSSYYSPNDNA (SEQ ID NO:4, 399-l), and CDR3: FYSGGGYYAGYFTL (SEQ ID NO:9, 399-h) and CDR sequences with up to two amino acid mutations as compared to SEQ ID NOs:4 and 9.

In some embodiments, the antibody comprises one or more of the following CDRs: CDR3: QSSYYSPNDNA (SEQ ID NO:4, 399-l), and CDR3: FYSGGGYYAGYFTL (SEQ ID NO:9, 399-h).

In some embodiments, the antibody comprises the following CDRs: CDR1: QASQSIGGNLA (SEQ ID NO:17, 399-l N31G), CDR2: LASYLAS (SEQ ID NO:3, 399-l), and CDR3: QSSYYSPNDNA (SEQ ID NO:4, 399-l).

In some embodiments, the antibody comprises the following CDRs: CDR1: GFSFDRNYWIA (SEQ ID NO:31, 399-h C35A), CDR2: AISAGGSGNTYYATWAKG (SEQ ID NO:35, 399-h C50A), and CDR3: FYSGGGYYAGYFTL (SEQ ID NO:9, 399-h).

In some embodiments, the antibody comprises one or more of the following CDRs: CDR1: QASQSIGGNLA (SEQ ID NO:17, 399-l N31G), CDR1: GFSFDRNYWIA (SEQ ID NO:31, 399-h C35A), CDR2: LASYLAS (SEQ ID NO:3, 399-l), CDR2: AISAGGSGNTYYATWAKG (SEQ ID NO:35, 399-h C50A), CDR3: QSSYYSPNDNA (SEQ ID NO:4, 399-l), and CDR3: FYSGGGYYAGYFTL (SEQ ID NO:9, 399-h).

In some embodiments, the antibody further comprises a light chain variable region with the following amino acids Phe at position 2, Asn at position 22, Gln at position 70 and Val at position 75, as indicated in SEQ ID NOs: 13-15.

In some embodiments, the antibody is a rabbit-derived antibody.

In some embodiments, the antibody is humanized.

In some embodiments, the antibody comprises an IgG1 Fc-region.

In some embodiments, the antibody has effector function.

In some embodiments, aspects of the invention relate to an isolated antibody comprising SEQ ID NO:15 (399-l N31G) and SEQ ID NO:20 (399-h, C35A V50A).

In some embodiments, aspects of the invention relate to an isolated antibody comprising a sequence that has at least 80% homology to SEQ ID NO:15 (399-l N31G) and a sequence that has at least 80% homology to SEQ ID NO:20 (399-h, C35A V50A).

In some embodiments, aspects of the invention relate to an isolated antibody comprising a sequence that has at least 90% homology to SEQ ID NO:15 (399-l N31G) and a sequence that has at least 90% homology to SEQ ID NO:20 (399-h, C35A V50A).

In some embodiments, aspects of the invention relate to an isolated antibody comprising a sequence that has at least 95% homology to SEQ ID NO:15 (399-l N31G) and a sequence that has at least 95% homology to SEQ ID NO:20 (399-h, C35A V50A).

In some embodiments, aspects of the invention relate to an isolated antibody comprising a sequence that has up to 10 mutations compared to SEQ ID NO:15 (399-l N31G) and a sequence that has up to 10 mutations compared to SEQ ID NO:20 (399-h, C35A V50A).

In some embodiments, aspects of the invention relate to an isolated antibody having the following light chain sequence:

(SEQ ID NO: 66)
AFQLTQSPSSLSASVGDRVTINCQASQSIGGNLAWYQQKPGKAPKLLIY

LASYLASGVPSRFSGSGSGTQFTLTVSSLQPEDFATYYCQSSYYSPNDN

AFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYAC

EVTHQGLSSPVTKSFNRGEC;

and/or the following heavy chain sequence:

(SEQ ID NO: 67)
QVQLVESGGGVVQPGRSLRLSCAASGFSFDRNYWIAWVRQAPGKGLEWV

AAISAGGSGNTYYATWAKGRFTISRDNSKNTLYLQMNSLRAEDTAVYYC

ARFYSGGGYYAGYFTLWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPG.

In some embodiments, the light chain signal sequence is MRVPAQLLGLLLLWLPGARC (SEQ ID NO:68).

In some embodiments, the heavy chain signal sequence is MDFGLSWVFLVLVLKGVQC (SEQ ID NO:69).

In some embodiments, aspects of the invention relate to an isolated humanized antibody comprising a light chain variable region with the following amino acids Phe at position 2, Asn at position 22, Gln at position 70 and Val at position 75, as indicated in SEQ ID NOs 13-15.

In some embodiments, aspects of the invention relate to a method for humanizing a rabbit monoclonal antibody, the method comprising introducing the following amino acids in the light chain variable region of a rabbit monoclonal antibody: Phe at position 2, Asn at position 22, Gln at position 70 and Val at position 75, as indicated in SEQ ID NOs 13-15.

In some embodiments, aspects of the invention relate to a method of treating a subject having one or more signs or symptoms of progressive multifocal leukoencephalopathy (PML), or having PML, the method comprising administering one or more of the antibodies described herein to a subject having one or more signs or symptoms of PML, or of having PML, in a therapeutically effective amount to treat PML.

In some embodiments, the antibody crosses the blood-brain barrier.

In some embodiments, the treatment results in a reduction in viral load, an improved EDSS score, an improved Karnofsky score, an improved MRI scan, or an improvement in cognition. In some embodiments, the subject is undergoing, or has been undergoing, immunotherapy treatment. In some embodiments, the subject is immunocompromised.

BRIEF DESCRIPTION OF THE DRAWINGS

The figures are illustrative only and are not required for enablement of the invention disclosed herein.

FIG. 3 provides an overview of the EC50, EC80 and EC90 of the antibodies against JCV and BKV in the various assays.

FIG. 4 shows the results of the ability of rabbit-derived monoclonal antibodies to bind the JCV-VP1 wild-type protein and the JCV-VP1 mutants L55F, S269F, Q271H, K60E and D66H.

FIG. 5 shows the results of binding studies of the rabbit-monoclonal 399 and the humanized antibodies BIIB048 (=H0L0), $H0_{V50A}$ $L2_{N31A}$ and $H0_{V50A}$ $L2_{N31A}$ to a number of wild-type and mutant JCV-VP1 using ELISA.

FIG. 6 shows the results of binding studies of the humanized antibodies BIIB048 (=H0L0), and $H0_{V50A}$ $L2_{N31A}$ to a number of wild-type and mutant JCV-VP1 using ELISA.

FIG. 7 provides an overview of the JCV VP1 combined mutation frequency.

FIG. 9 shows an overview of virus preps for infectivity assay.

FIG. 10 shows an overview of viral mutant infectivity assay.

FIG. 11 shows the results of a viral mutant infectivity assay as shown by Western blot.

FIG. 12 shows the results of a viral mutant infectivity assay as shown by Western blot.

FIG. 13 shows the results of a viral mutant infectivity assay as shown by Western blot.

FIG. 14 shows the results of a viral mutant infectivity assay as shown by Western blot.

FIG. 15 shows an overview of JCV-VLP1 binding ELISA assay.

FIG. 16 shows an overview of JCV-VLP1 binding ELISA assay.

FIG. 17 shows the results of the JCV-VLP1 binding ELISA assay.

DETAILED DESCRIPTION OF THE INVENTION

Figure 1:
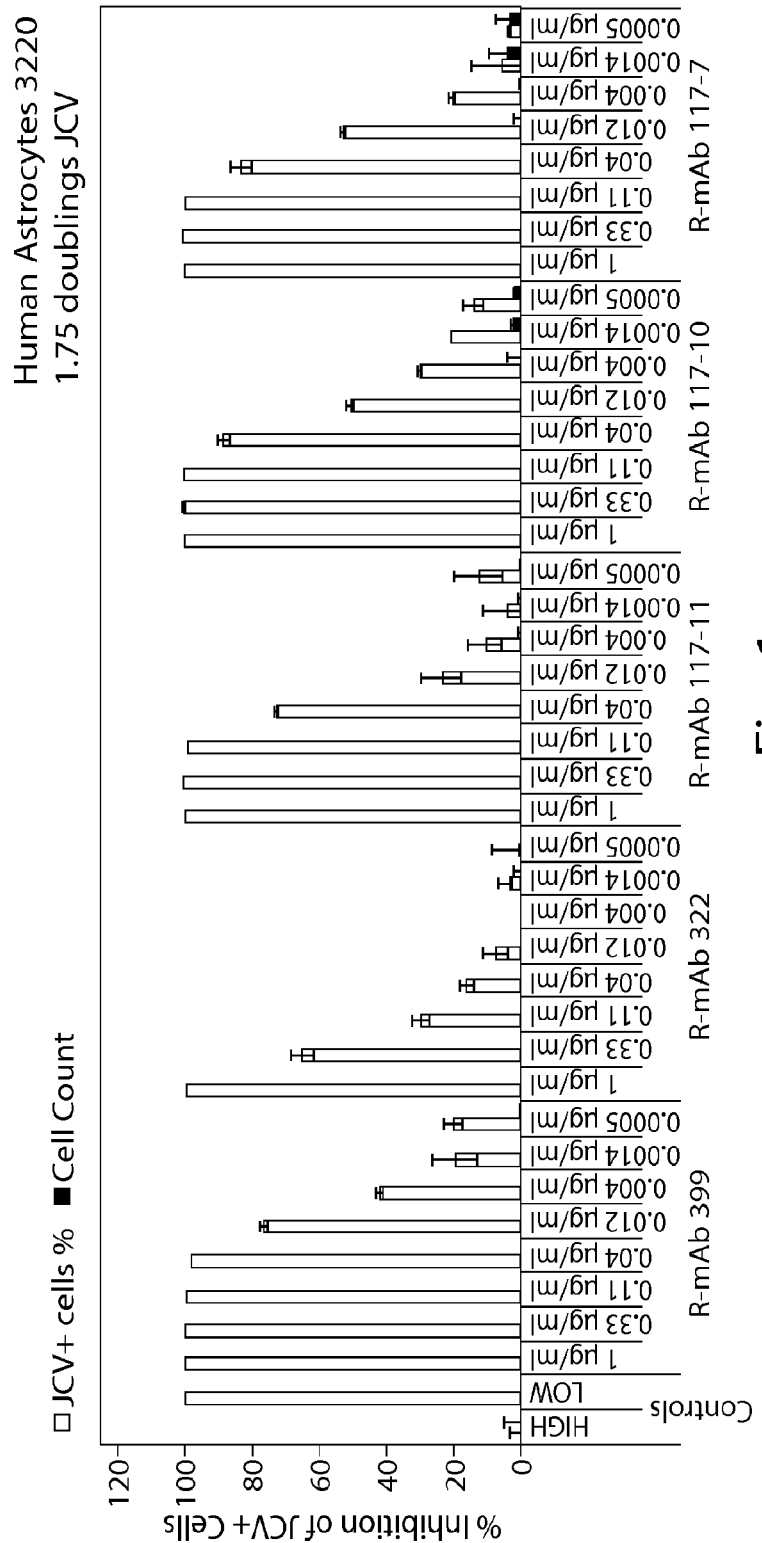
FIG. 1 shows the results of the ability of rabbit-derived monoclonal antibodies to neutralize JCV and BKV virus in a human astrocytes infectivity inhibition assay.
Figure 1:
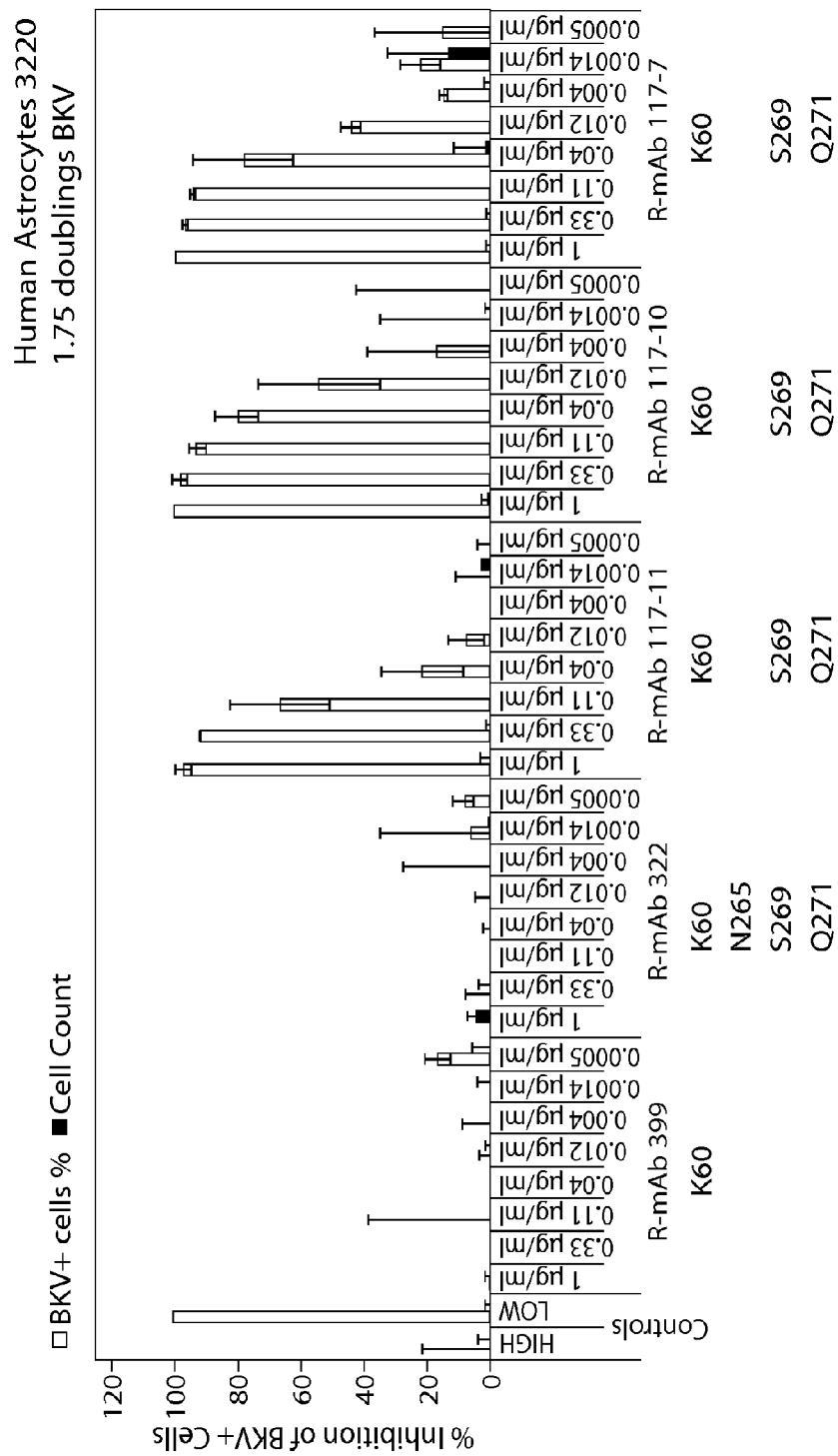

In some embodiments, aspects of the invention relate to antibodies that bind to one or more JC Virus (JCV) proteins. In some embodiments, JCV-binding antibodies are neutralizing antibodies that reduce or inhibit one or more JCV functions. In some embodiments, a neutralizing antibody inhibits JCV replication, proliferation, and/or infectivity. In some embodiments, a neutralizing antibody induces viral clearance by the immune system, blocks virus receptor interactions, and/or disrupts virus capsids.

In some embodiments, antibodies that bind to a JCV coat protein, for example the JCV VP1 protein, are neutralizing antibodies. In some embodiments, antibodies that bind to the sialic acid binding pocket of the JCV VP1 protein are neutralizing antibodies. Surprisingly, a JCV neutralizing antibody that binds to VP1 can be effective against two or more different JCV variants, including variants that have one or more amino acid sequence changes within the sialic acid binding pocket of the VP1 protein.

A neutralizing antibody can be useful to help prevent, manage, and/or treat one or more conditions associated with a JCV infection. JCV infection is highly prevalent in humans. Primary infection with JCV can occur asymptomatically during childhood. JCV can be disseminated throughout the body, probably through viraemia and it is thought that JCV often persists mostly in brain and renal tissue. While infection by JCV is asymptomatic in most subjects, infection may result in serious conditions (like PML) and even death in some subjects. Subjects most susceptible to PML are subjects that are immuno-compromised (e.g., AIDS patients) or subjects undergoing treatment with immuno-suppressants (for instance after organ transplant or to treat an inflammation related condition such as multiple sclerosis). Neutralizing antibodies described herein can be used to treat patients that are at risk for developing a JCV associated condition. In some embodiments, an immuno-compromised patient can be treated with a JCV neutralizing antibody to reduce the risk of PML or other JCV-associated condition even if the treatment does not clear all JCV from the patient. It should be appreciated that by inhibiting JCV proliferation (e.g., JCV replication and/or dissemination in a subject), the risk of JCV-associated conditions can be reduced and/or managed as part of a treatment program for an immuno-compromised patient. In some embodiments, a patient receiving an immuno-suppressive drug (e.g., Tysabri) can be monitored for one or more signs or symptoms of a JCV-associated condition (e.g., PML). If a sign or symptom is detected, a JCV-neutralizing antibody can be administered. In some embodiments, the immuno-suppressive treatment also can be suspended or reduced to allow the patient's immune system to recover and counter a JCV infection or proliferation. However, it should be appreciated that a JCV-neutralizing antibody can be used in different therapeutic methods to treat or prevent JCV infections and/or JCV-associated conditions as described in more detail herein. It also should be appreciated that a JCV-neutralizing antibody can be used as a reagent, for example an assay reagent, to detect the presence of a JCV protein or virus in a sample. In some embodiments, antibodies described herein can be used as virus detection or quantification reagents.

In some embodiments, certain JCV variants are associated with an increased risk for a disease or disorder caused by the JCV infection. For example, certain mutations in the sialic acid binding pocket of the JCV VP1 protein have been associated with an increased risk for PML. In some embodiments, a JCV-neutralizing antibody is specific for one or more JCV variants. In some embodiments, a JCV-neutralizing antibody binds to a plurality of JCV variants with sufficient affinity to be therapeutically effective against those variants. In some embodiments, a JCV-neutralizing antibody binds to the sialic acid binding pocket of the JCV virus. It should be appreciated that the sialic acid binding pocket is reported to be the receptor interaction domain of the virus. In some embodiments, the sialic acid binding pocket includes amino acids 55-76 and amino acids 265-273 of JCV (See e.g., Gee et al., 2004, JBC 279: 49172-49176). In some embodiments, a JCV-neutralizing antibody binds to a plurality of JCV variants each having one or more amino acid changes within the sialic acid binding pocket. However, in some embodiments, certain amino acid changes within the sialic acid binding pocket reduce binding (and inhibition) by a JCV-neutralizing antibody. In some embodiments, a subject is screened for signs of a JCV infection. In some embodiments, a subject is screened for infection by a JCV variant. In some embodiments, a subject (for example a subject known to have a JCV infection) can be monitored for the appearance of one or more higher risk JCV variants. A positive result for JCV infection and/or the presence of certain JCV variants in a patient sample can be used as a basis for initiating treatment with a JCV-neutralizing antibody. However, it should be appreciated that in some embodiments a JCV-neutralizing antibody can be administered to a patient on the basis of an increased risk for JCV infection or proliferation and/or an increased risk for a JCV-associated condition, regardless of whether a JCV detection assay has been performed on the patient.

A reduction in JC Virus replication, proliferation, infectivity, and/or any other function caused by an antibody can be a measured (e.g., using an in vitro and/or in vivo assay) by comparing one or more JCV functions in the presence versus the absence of the antibody. In some embodiments, a neutralizing antibody can result in a reduction in one or more virus functions (e.g., replication, proliferation, infection, etc.) by about 5%, about 10%, about 20%, about 30%, about 40%, about 50%, about 60%, about 70%, about 80%, about 90%, about 95%, or more.

Antibodies:

In some embodiments, an antibody is a monoclonal antibody that is raised against a JCV VLP. In some embodiments, the antibody is specific for JCV. In some embodiments, the antibody is specific for JCV VP1.

In some embodiments, a neutralizing antibody that is specific for JCV has a neutralizing effect on JCV activity that is significantly higher than its neutralizing effect on the activity of one or more other viruses, for example, of a related virus (e.g., BK virus). However, in some embodiments, a neutralizing antibody may bind to one or more viruses with sufficient affinity to be useful to treat one or more different viral infections.

In some embodiments, the antibody is a monoclonal antibody. In some embodiments, the antibody is humanized. In some embodiments, an antibody has the sequence of R399 or R411 as described herein.

In some embodiments, an antibody comprises one or more of the following CDR sequences: CDR1: SEQ ID NOs:2, 7, 16-18, 31-33; CDR2: SEQ ID NOs:3, 8, 34-37; CDR3: SEQ ID NOs:4, 9.

In some embodiments, an antibody comprises one or more of the following CDR sequences: CDR1: SEQ ID NOs:40, 45, 61-63; CDR2: SEQ ID NOs:41, 46, 64, 65; CDR3: SEQ ID NOs:42, 47.

In some embodiments, an antibody comprises one or more of the following CDR sequences: CDR1: QASQSIGX-NLA (SEQ ID NO:18, 399-l N31X), CDR1: GFSFDRNY-WIX (SEQ ID NO:33, 399-h C35X), CDR2: LASYLAS (SEQ ID NO:3, 399-l), CDR2: XISAGGSGNTYYAT-WAKG (SEQ ID NO:37, 399-h C50X), CDR3: QSSYYSPNDNA (SEQ ID NO:4, 399-l), CDR3: FYSGGGYYAGYFTL (SEQ ID NO:9, 399-h), and CDR sequences with up to two amino acid mutations as compared to SEQ ID NOs:18, 33, 3, 37, 4 and 9.

In some embodiments, an antibody comprises one or more of the following CDR sequences: CDR1: QASQSIG-GNLA (SEQ ID NO:17, 399-l N31G), CDR1: GFSFDRNY-WIA (SEQ ID NO:31, 399-h C35A), CDR2: LASYLAS (SEQ ID NO:3, 399-l), CDR2: AISAGGSGNTYYAT-WAKG (SEQ ID NO:35, 399-h C50A), CDR3: QSSYYSPNDNA (SEQ ID NO:4, 399-l), CDR3: FYSGGGYYAGYFTL (SEQ ID NO:9, 399-h), and CDR sequences with up to two amino acid mutations as compared to SEQ ID NOs:17, 31, 3, 35, 4 and 9.

In some embodiments, an antibody comprises one or more of the following CDR sequences: CDR1: QASQSIG-GNLA (SEQ ID NO:17, 399-l N31G), CDR1: GFSFDRNY-WIA (SEQ ID NO:31, 399-h C35A), CDR2: LASYLAS (SEQ ID NO:3, 399-l), CDR2: AISAGGSGNTYYAT-WAKG (SEQ ID NO:35, 399-h C50A), CDR3: QSSYYSPNDNA (SEQ ID NO:4, 399-l), and CDR3: FYSGGGYYAGYFTL (SEQ ID NO:9, 399-h).

In some embodiments, an antibody comprises one or more of the following CDRs: CDR3: QSSYYSPNDNA (SEQ ID NO:4, 399-l), and CDR3: FYSGGGYYAGYFTL (SEQ ID NO:9, 399-h) and CDR sequences with up to two amino acid mutations as compared to SEQ ID NOs:4 and 9.

In some embodiments, an antibody comprises the following CDRs: CDR1: QASQSIGGNLA (SEQ ID NO:17, 399-l N31G), CDR2: LASYLAS (SEQ ID NO:3, 399-l), and CDR3: QSSYYSPNDNA (SEQ ID NO:4, 399-l).

In some embodiments, an antibody comprises the following CDRs: CDR1: GFSFDRNYWIA (SEQ ID NO:31, 399-h C35A), CDR2: AISAGGSGNTYYATWAKG (SEQ ID NO:35, 399-h C50A), and CDR3: FYSGGGYYAGYFTL (SEQ ID NO:9, 399-h).

In some embodiments, an antibody comprises one or more of the following CDRs: CDR1: QASQSIGGNLA (SEQ ID NO:17, 399-l N31G), CDR1: GFSFDRNYWIA (SEQ ID NO:31, 399-h C35A), CDR2: LASYLAS (SEQ ID NO:3, 399-l), CDR2: AISAGGSGNTYYATWAKG (SEQ ID NO:35, 399-h C50A), CDR3: QSSYYSPNDNA (SEQ ID NO:4, 399-l), and CDR3: FYSGGGYYAGYFTL (SEQ ID NO:9, 399-h).

In some embodiments, an antibody has the following heavy chain CDR3: FYSGGGYYAGYFTL (SEQ ID NO:9, 399-h), and/or the following light chain CDR3: QSSYYSPNDNA (SEQ ID NO:4, 399-l).

In some embodiments, an antibody has the following heavy chain CDR2: AISAGGSGNTYYATWAKG (SEQ ID NO:35, 399-h C50A), and/or the following light chain CDR2: LASYLAS (SEQ ID NO:3, 399-l).

In some embodiments, an antibody has the following heavy chain CDR1: GFSFDRNYWIA (SEQ ID NO:31, 399-h C35A), and/or the following light chain CDR1: CDR1: QASQSIGGNLA (SEQ ID NO:17, 399-l N31G).

In some embodiments, one or more humanization changes have been made: position 8 in CDR1 of the variable light chain, see e.g., SEQ ID NOs: 16-18.

In some embodiments, an antibody has a heavy chain variable region having one of the following SEQ ID NOs:6, 19-30. In some embodiments, an antibody has a light chain variable region having one of the following SEQ ID NOs:1, 11-15.

In some embodiments, an antibody has a heavy chain variable region having one of the following SEQ ID NOs:43, 51-60. In some embodiments, an antibody has a light chain variable region having one of the following SEQ ID NOs: 38, 48-50.

In some embodiments, an antibody has a heavy chain variable region having SEQ ID NO:20. In some embodiments, an antibody has a light chain variable region having SEQ ID NO:15.

In some embodiments, one or more of the following humanization changes has been made in a light chain variable region at the following amino acids Phe at position 2, Asn at position 22, Gln at position 70 and Val at position 75, as indicated in SEQ ID NOs: 13-15. In some embodiments, one or more of the following humanization changes has been made in a light chain variable region at the following amino acids Phe at position 2, Asn at position 22, Gln at position 70 and Val at position 75, as indicated in SEQ ID NOs: 13-15.

In some embodiments, an antibody may be substantially a full length VP-1 binding antibody or a functional fragment thereof. For example, if a fragment of a VP-1 binding antibody is sufficient to allow specific binding by an antibody that specifically binds a VP-1 binding antibody it is a functional VP-1 binding antibody and may be used in the methods and kits of the invention. In some embodiments, an antibody fragment can be used if it provides sufficient binding to inhibit JCV function and/or to be useful as a detection agent for JCV. One of ordinary skill in the art will be able to identify VP-1 binding antibody fragments and determine whether a VP-1 binding antibody fragment is a functional VP-1 binding antibody fragment using only routine procedures and binding assays (e.g., competition assays using a substantially full length VP-1 binding antibody described herein.

In some embodiments, an antibody may be a chimeric antibody that contains a variable region (e.g., a humanized variable region) from a first species (e.g., a rabbit) and an Fc region from a second species (e.g., a human). As will be apparent to one of ordinary skill in the art, the present invention also provides for F(ab')2, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences.

In certain embodiments, a JCV neutralizing antibody may be an anti-VP1 single-chain antibody, a single-domain antibody, or a Nanobody™. Characteristics of each of these antibody types and methods for their use are well known in the art. Nanobodies™ are the smallest functional fragments of antibodies and are derived from naturally occurring single-chain antibodies (see Ablynx, Belgium; ablynx.com). Nanobody™ technology was developed following the discovery that camelidae (camels and llamas) possess a unique repertoire of fully functional antibodies that lack light chains. Nanobody™ structure consists of a single variable domain (VHH), a hinge region, and two constant domains (CH2 and CH3). The cloned and isolated VHH domain is a stable polypeptide harboring the full antigen-binding capacity of the original heavy chain. Nanobodies™ combine the features of conventional antibodies with features of small molecule drugs. Nanobodies™ show high target specificity and low inherent toxicity. Additionally, Nanobodies™ are very stable, can be administered by means other than injection, and are easy to manufacture. In certain embodiments, a therapeutic JCV neutralizing antibody, an immobilization moiety, and/or a detection moiety may be a humanized Nanobody™.

In some embodiments, an exemplary JCV neutralizing antibody has one or more CDRs, e.g., all three Heavy Chain (HC) CDRs and/or all three Light Chain (LC) CDRs of a particular antibody disclosed herein, or CDRs that are, in sum, at least 80, 85, 90, 92, 94, 95, 96, 97, 98, or 99% identical to such an antibody, e.g., CDR1: SEQ ID NOs:2, 7, 16-18, 31-33; CDR2: SEQ ID NOs:3, 8, 34-37; CDR3: SEQ ID NOs:4, 9, and CDR1: SEQ ID NOs:40, 45, 61-63; CDR2: SEQ ID NOs:41, 46, 64, 65; CDR3: SEQ ID NOs:42, 47. In some embodiments, an exemplary JCV neutralizing antibody has one, two, three, four, five or six of the CDRs, e.g., all three Heavy Chain (HC) CDRs and/or all three Light Chain (LC) CDRs of a particular antibody disclosed herein, In some embodiments, an exemplary JCV neutralizing antibody has one or more CDRs, e.g., all three Heavy Chain (HC) CDRs and/or all three Light Chain (LC) CDRs of a particular antibody disclosed herein, or CDRs that include one, up to two, up to three, up to four, up to five, up to six, up to seven, up to eight, up to nine or up to ten amino acid changes compared to e.g., CDR1: SEQ ID NOs:2, 7, 16-18, 31-33; CDR2: SEQ ID NOs:3, 8, 34-37; CDR3: SEQ ID NOs:4, 9, and CDR1: SEQ ID NOs:40, 45, 61-63; CDR2: SEQ ID NOs:41, 46, 64, 65; CDR3: SEQ ID NOs:42, 47. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 70, 80, 85, 90, 92, 95, 97, 98, 99, or 100% identical to the amino acid sequence of the HC and/or LC variable domain of an antibody described herein, e.g., SEQ ID NOs 1, 6, 11-15, 19-30 and 43, 51-60, 38, 48-50. The amino acid sequence of the HC and/or LC variable domain sequence can differ by at least one amino acid, but no more than ten, eight, six, five, four, three, or two amino acids from the corresponding sequence of an antibody described herein, e.g., SEQ ID NOs 1, 6, 11-15, 19-30 and 43, 51-60, 38, 48-50. For example, the differences may be primarily or entirely in the framework regions.

The amino acid sequences of the HC and LC variable domain sequences can be encoded by a sequence that hybridizes under high stringency conditions to a nucleic acid sequence described herein or one that encodes a variable domain or to a nucleic acid encoding an amino acid sequence described herein. In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of an antibody described herein. In one embodiment, one or more heavy or light chain framework regions (e.g., HC FR1, FR2, and FR3) are at least 70, 80, 85, 90, 95, 96, 97, 98, or 100% identical to the sequence of corresponding framework regions from a human germline antibody.

Calculations of "homology" or "sequence identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

The skilled artisan will realize that conservative amino acid substitutions may be made in JCV neutralizing antibodies to provide functionally equivalent variants of these antibodies, e.g., the variants retain the functional capabilities of inhibiting one or more JCV functions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants of JCV neutralizing antibodies include conservative amino acid substitutions of in the amino acid sequences of proteins disclosed herein. Conservative substitutions of amino acids include substitutions made amongst amino acids within the following groups: (a) M, I, L, V; (b) F, Y5 W; (c) K, R, H; (d) A, G; (e) S, T; (f) Q, N; and (g) E, D.

As used herein, the term "hybridizes under high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and non-aqueous methods are described in that reference and either can be used. High stringency hybridization conditions can include hybridization in 6×SSC at about 45° C., followed by one or more washes in 0.2×SSC, 0.1% SDS at 65° C., or substantially similar conditions.

Antibodies can be tested for a functional property, for example, JCV neutralization, e.g., as described herein or using other techniques for evaluating JCV replication, propagation, infectivity, and/or other function.

In some embodiments, a combination of two or more different antibodies may be used. In some embodiments, one or more antibodies may be used in combination with one or more other agents. In some embodiments, tetravalent antibodies, antibodies coupled to blood brain barrier transporters, antibodies coupled to contrast dye reagents, and/or radiolabelled antibodies can be used (e.g., as markers of JCV presence in patients).

Obtaining Antibodies and Antigen Binding Fragments:

JCV neutralizing antibodies can be generated by immunization, e.g., using an animal such as a rabbit. A JCV VLP, or a VLP protein (e.g., VP1) can be used as an immunogen. In some embodiments, a VLP or VLP protein having a wild-type or normal sequence can be used. In some embodiments, a VLP or VLP protein having one or more mutations (for example in the sialic acid binding pocket of VP1) can be used as an immunogen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Antibodies or immunoglobulins include broad classes of polypeptides that can be distinguished biochemically. Those skilled in the art will appreciate that heavy chains are classified as gamma, mu, alpha, delta, or epsilon, with some subclasses among them (e.g., gamma1-gamma4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and JCV neutralizing antibodies of different classes can be obtained or engineered as described herein. It should be appreciated that all immunoglobulin classes are within the scope of the present invention. However, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda. Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As described herein, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a beta-sheet conformation and the CDRs form loops which connect, and in some cases form part of, the beta-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

It should be appreciated that antibodies obtained as described herein can be altered to remove or replace one or more CDRs. In some embodiments, antigen binding fragments can be generated that retain antigen specificity but that lack one or more of the six CDRs of a full-length antibody. Alternatively, one or more CDRs from an antibody can be retained (for example CDR3) and one or more of the other CDRs can be engineered and or replaced with a different CDR, for example, to alter antigen binding specificity and/or affinity.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in a neutralizing antibody or antigen-binding fragment, variant, or derivative thereof of the present invention are according to the Kabat numbering system.

In camelid species, the heavy chain variable region, referred to as VHH, forms the entire antigen-binding domain. The main differences between camelid VHH variable regions and those derived from conventional antibodies (VH) include (a) more hydrophobic amino acids in the light chain contact surface of VH as compared to the corresponding region in VHH, (b) a longer CDR3 in VHH, and (c) the frequent occurrence of a disulfide bond between CDR1 and CDR3 in VHH.

As described herein, JCV binding antibodies or antigen-binding fragments, variants, or derivatives thereof include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to neutralizing antibodies disclosed herein). ScFv molecules are known in the art and are described, e.g., in U.S. Pat. No. 5,892,019. JCV neutralizing immunoglobulin or antibody molecules can be of any type (e.g., IgG, IgE, IgM, IgD, IgA, and IgY), class (e.g., IgG1, IgG2, IgG3, IgG4, IgA1 and IgA2) or subclass of immunoglobulin molecule.

JCV neutralizing antibody fragments, including single-chain antibodies, may comprise the variable region(s) alone or in combination with the entirety or a portion of the following: hinge region, CH1, CH2, and CH3 domains. Also, JCV neutralizing antigen-binding fragments can comprise any combination of variable region(s) with a hinge region, CH1, CH2, and CH3 domains.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

As used herein, the term "light chain portion" includes amino acid sequences derived from an immunoglobulin light chain. Preferably, the light chain portion comprises at least one of a VL or CL domain.

Neutralizing antibodies, or antigen-binding fragments, variants, or derivatives thereof disclosed herein may be described or specified in terms of the epitope(s) or portion(s) of an antigen, e.g., a target polypeptide of the JCV VP1 protein that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In some embodiments, a peptide or polypeptide epitope recognized by neutralizing antibodies described herein contains a sequence of at least 4, at least 5, at least 6, at least 7, more preferably at least 8, at least 9, at least 10, at least 15, at least 20, at least 25, or between about 15 to about 30 contiguous or non-contiguous amino acids of a JCV VLP protein (e.g., VP1). (See e.g., WO2010/090757)

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Neutralizing antibodies or antigen-binding fragments, variants or derivatives thereof described herein may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Neutralizing antibodies or antigen-binding fragments, variants or derivatives thereof described herein may also be described or specified in terms of their binding affinity to a polypeptide. For example, a JCV neutralizing antibody may bind to a JCV peptide (e.g., a VP1 peptide) with a dissociation constant or Kd less than $10^{-2}$M, $10^{-3}$M, $10^{-4}$M, $10^{-5}$M, $10^{-6}$M, $10^{-7}$M, $10^{-8}$M, $10^{-9}$M, $10^{-10}$M, $10^{-11}$M, $10^{-12}$M, $10^{-13}$M, $10^{-14}$M, or $10^{-15}$M.

Neutralizing antibodies or antigen-binding fragments, variants or derivatives thereof described herein may be "multispecific," e.g., bispecific, trispecific or of greater multispecificity, meaning that it recognizes and binds to two or more different epitopes present on one or more different antigens (e.g., proteins) at the same time. Thus, whether a neutralizing antibody is "monospecfic" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

Humanization:

In some embodiments, an animal antibody (e.g., rabbit antibody) can be modified, for example by, exchanging the Fc region with an Fc region from a different species (for example with a human Fc region). In some embodiments, one or more humanization changes also may be made (for example in one or more of the framework regions of the antibody).

In some embodiments, antibodies described herein may be engineered, by partial framework region replacement and sequence changing. In some embodiments, CDRs are derived from an antibody of a different class and/or a different species than the framework regions. In some embodiments, an engineered antibody contains one or more "donor" CDRs from a non-human antibody of known specificity that are grafted into a human heavy or light chain framework region. It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

EP 239 400 (Winter et al.) describes altering antibodies by substitution (within a given variable region) of their complementarity determining regions (CDRs) for one species with those from another. CDR-substituted antibodies are predicted to be less likely to elicit an immune response in humans compared to true chimeric antibodies because the CDR-substituted antibodies contain considerably less non-human components. (Riechmann et al., 1988, Nature 332, 323-327; Verhoeyen et al., 1988, Science 239, 1534-1536). Typically, CDRs of a murine antibody substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes are co-expressed in mammalian cells to produce soluble humanized antibody.

Queen et al., 1989 Proc Natl Acad Sci USA. December; 86(24): 10029-33 and WO 90/07861 have described a process that includes choosing human V framework regions by computer analysis for optimal protein sequence homology to the V region framework of the original murine antibody, and modeling the tertiary structure of the murine V region to visualize framework amino acid residues which are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271) utilize, as standard, the V region frameworks derived from NEWM and REI heavy and light chains respectively for CDR-grafting without radical introduction of mouse residues. An advantage of using the Tempest et al., approach to construct NEWM and REI based humanized antibodies is that the three-dimensional structures of NEWM and REI variable regions are known from x-ray crystallography and thus specific interactions between CDRs and V region framework residues can be modeled. However, it should be appreciated that similar approaches may be based on one or more other known antibody structures (e.g., based on one or more Fab structures). In some embodiments, a human germline framework may be used (e.g., as described for antibody 399 herein).

In some embodiments, a rabbit VH region (e.g., the 399 antibody described herein) has a framework 1 and/or a framework 3 that is shorter than the corresponding human framework regions. In some embodiments, corresponding amino acid deletions can be made in humanized variants of rabbit antibodies. In some embodiments, these deletions do not have a large effect on affinity. For example, similar binding affinities are found for H4 (human-like, with no deletions) and H9 (more rabbit-like, with deletions).

In some embodiments, a rabbit antibody may be modified (e.g., as part of a humanization process) by removing one or more disulfide bonds. Accordingly, one or more Cys residues in the VL and CL domains can be replaced with human residues in some embodiments without a loss of function. A non-limiting example of this is described herein (e.g., see the Examples). There also is a disulfide bond between CDR H1 and CDR H2 (residues 35a and 50) that is conserved in many rabbit VH domains (approximately one-third of VH sequences). In some embodiments, one or both of the Cys residues of this pair can be replaced with other residues without loss of affinity.

Non-human antibodies can be modified to include substitutions that insert human immunoglobulin sequences, e.g., consensus human amino acid residues at particular positions, e.g., at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H5 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

Antibody Production:

Monoclonal (e.g., monoclonal rabbit, mouse, chimeric, humanized, fully human, etc.) JCV neutralizing antibodies can be produced using techniques known in the art. In some embodiments, fully human antibodies can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236. U.S. Pat. No. 5,798,230. Large nonimmunized human phage display libraries may also be used to isolate high affinity antibodies that can be developed as human therapeutics using standard phage technology (see, e.g., Vaughan et al, 1996 Nat Biotechnol. March; 14(3):309-14; Hoogenboom et al. (1998) Immunotechnology 4:1-20; and Hoogenboom et al. (2000) Immunol Today 2:371-8; US Published Patent Application No. 2003-0232333). Antibodies can be produced in prokaryotic and eukaryotic cells. In some embodiments, antibodies (e.g., scFvs) are expressed in a yeast cell such as Pichia (see, e.g., Powers et al. (2001) J Immunol Methods. 251:123-35), Hanseula, or Saccharomyces.

In some embodiments, antibodies, particularly full length antibodies, e.g., IgGs, are produced in mammalian cells. Exemplary mammalian host cells for recombinant expression include Chinese Hamster Ovary (CHO cells) (including dhfr− CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NSO myeloma cells and SP2 cells, COS cells, K562, and a cell from a transgenic animal, e.g., a transgenic mammal. For example, a mammary epithelial cell can be used.

In addition to the nucleic acid sequence(s) encoding the immunoglobulin domain, recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). Exemplary selectable marker genes include the dihydrofolate reductase (DHFR) gene (for use in dhfr− host cells with methotrexate selection/ amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/ amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and -recover the antibody from the culture medium. For example, some antibodies can be isolated by affinity chromatography with a Protein A or Protein G. In some embodiments, rabbit antibody variable regions were cloned and expressed in CHO cells.

Antibodies also can include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some antibodies that include an Fc domain, the antibody production system may be designed to synthesize antibodies in which the Fc region is glycosylated. For example, the Fc domain of IgG molecules is glycosylated at asparagine 297 in the CH2 domain. This asparagine is the site for modification with biantennary-type oligosaccharides. This glycosylation participates in effector functions mediated by Fcγ receptors and complement C1q (Burton and Woof (1992) Adv. Immunol. 51:1-84; Jefferis et al. (1998) Immunol. Rev. 163:59-76). The Fc domain can be produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

In certain embodiments, rather than humanizing an existing antibody or antigen binding fragment from a different species, an animal that contains immunoglobulin producing cells having natural, human, or partially human immunoglobulin loci can be immunized. In some embodiments, the non-human animal includes at least a part of a human immunoglobulin gene. For example, it is possible to engineer animal strains that are deficient in animal antibody production using large fragments of the human Ig loci. Using the hybridoma technology, antigen-specific monoclonal antibodies derived from the genes with the desired specificity may be produced and selected.

Therapeutic Applications:

In some embodiments, a neutralizing antibody described herein may be administered to a subject who is undergoing a therapy with an immunosuppressive drug. In some embodiments, a JCV neutralizing antibody may be used to prevent the development or progression of PML in a subject that is undergoing treatment for multiple sclerosis (MS). For example, a subject undergoing treatment with natalizumab or a related VLA-4 binding antibody may be a candidate for treatment with a JCV neutralizing antibody.

Natalizumab and related VLA-4 binding antibodies are described, e.g., in U.S. Pat. No. 5,840,299. mAb 21.6 and HP 1/2 are exemplary murine monoclonal antibodies that bind VLA-4. Natalizumab is a humanized version of murine mAb 21.6 (see, e.g., U.S. Pat. No. 5,840,299). A humanized version of HP1/2 has also been described (see, e.g., U.S. Pat. No. 6,602,503). Several additional VLA-4 binding monoclonal antibodies, such as HP2/1, HP2/4, L25 and P4C2, are described (e.g., in U.S. Pat. No. 6,602,503; Sanchez-Madrid et al., 1986 Eur. J. Immunol, 16:1343-1349; Hemler et al., 1987 J. Biol. Chem. 2:11478-11485; Issekutz and Wykretowicz, 1991, J. Immunol, 147: 109 (TA-2 mab); Pulido et al, 1991 J. Biol. Chem., 266(16):10241-10245; and U.S. Pat. No. 5,888,507). Many useful VLA-4 binding antibodies interact with VLA-4 on cells, e.g., lymphocytes, but do not cause cell aggregation. However, other anti-VLA-4 binding antibodies have been observed to cause such aggregation. HP1/2 does not cause cell aggregation. The HP1/2 MAb (Sanchez-Madrid et al., 1986 Eur. J. Immunol., 16:1343-1349) has an extremely high potency, blocks VLA-4 interaction with both VCAM1 and fibronectin, and has the specificity for epitope B on VLA-4. This antibody and other B epitope-specific antibodies (such as B1 or B2 epitope binding antibodies; Pulido et al., 1991 J. Biol. Chem., 266(16):10241-10245) represent one class of useful VLA-4 binding antibodies.

In some embodiments, a subject is human. In some embodiments, a subject is a non-human animal, for example a non-human mammal (e.g., mouse, rat, rabbit, goat, etc.).

Applications:

In some embodiments, a neutralizing antibody can be administered to a subject to prevent or treat a JC Virus infection, and/or to prevent or treat PML.

In some embodiments, aspects of the invention relate to antibody compositions that inhibit JC Virus activity, for example, that inhibit one or more of viral proliferation (e.g., viral replication), mutation rate, and infectivity. In some embodiments, such compositions can be used to treat or suppress conditions associated with JC Virus activity in subjects that are infected with a JC Virus, or to lower the risk of infection with the JC Virus. Such compositions may be used to prevent JCV viral infection, to prevent an increase in JCV viral activity (e.g., active JCV infection of the brain), to prevent JC Virus proliferation, to prevent symptoms associated with viral infection, to treat a subject infected with a JC Virus, or treat a subject at risk of infection with a JC Virus, or to treat a subject that has developed a disease or condition associated with infection by a JC Virus (e.g., PML). Compositions of the invention also may be administered to a subject at risk of a viral infection or at risk of an increase in viral activity (e.g., viral proliferation, for example in the brain or CNS), regardless of whether the subject is actually known to have been exposed to, or infected by, the virus.

In some embodiments, one or more antibody compositions can be administered to subjects that have a compromised immune system. It should be appreciated that a subject's immune system may be compromised due to treatment with an immunosuppressive therapeutic agent and/or due to a disease or condition that impacts the immune system. In some embodiments, one or more antibody compositions can be administered to a subject that is at risk of PML due to a compromised immune system, regardless of whether the subject is known to be infected with JCV or known to have been exposed to JCV. Accordingly, compositions of the invention may be administered to subjects that are receiving an immunosuppressive treatment for a disease or condition. In some embodiments, compositions of the invention may be administered to multiple sclerosis (MS) patients that are being treated with one or more immunosuppressive agents (e.g., natalizumab). However, in some embodiments, compositions of the invention may be administered to subjects that have a weakened immune system caused by a disease or condition itself, rather than by an immunosuppressive treatment. For example, subjects infected with an immuno-compromising pathogen (e.g., a virus such as HIV) may be treated with one or more antibody compositions described herein.

It should be appreciated that while the JCV status of a subject need not be known, it may be useful to know the status in some embodiments. In some embodiments, the efficacy of such treatment or therapy may be monitored by detecting and/or monitoring the presence of JCV in a subject.

In some embodiments, one or more antibody compositions can be administered to a subject before, during, and/or after the subject receives and immunomodulatory therapy (e.g., a treatment that inhibits the immune system of the subject). Accordingly, in some embodiments one or more compounds described herein as being effective to inhibit JC Virus replication may be administered to a subject prior to initiation of an immunomodulatory therapy. For example, a therapeutic regimen of one or more compositions of the invention may be initiated prior to an immunomodulatory treatment against a disease or in preparation for a transplant in to prevent or reduce any risk of JC Virus replication or proliferation associated with the immunomodulatory treatment.

In some embodiments, one or more compositions of the invention may be administered alone or in combination with other compositions described herein or along with other therapeutic agents (e.g., one or more immunosuppressive therapeutic agents). Compositions of the invention may be provided (e.g., administered) in pharmaceutical preparations. Compositions of the invention may be provided in kits.

In some embodiments, a subject that is being treated with (or that is going to start a treatment with) an immunosuppressive agent is tested for one or more indicia of JCV infection. If one or more indicia of JCV infection are detected, the subject may be evaluated for the presence of one or more JCV variants associated with PML as described herein. If no indicia for JCV are detected, the subject may be monitored over time, e.g., every 4 weeks, monthly, every three months, every 4 months, every 6 months, or every 12 months, for the presence of any indicia of JCV infection. If a JCV infection is detected, the subject may be further evaluated for the presence of one or more JCV variants. If a JCV variant associated with increased PML risk is detected, the subject may be further monitored to detect any early signs of PML and/or the treatment regimen may be altered as described in more detail herein.

In some embodiments, a neutralizing antibody can be useful to slow the progression of a condition (e.g., PML) that is associated with a JCV infection. In some embodiments, a delay in the progression of PML or other condition associated with JCV allows a subject's immune response to fight the JCV infection. For example, if a subject undergoing immunotherapy or treatment with a drug that is immunosuppressive, is diagnosed as having a JCV infection, and/or as having one or more signs or symptoms of PML (e.g., early stage PML), then the subject can be treated by administering one or more antibody compositions described herein. In some embodiments, treatment with the immunotherapy or drug that is immunosuppressive is reduced or stopped during the time that the JCV neutralizing antibody is administered. This can allow the immune system of the subject to recover and help fight off the JCV infection or disease progression.

Nucleic Acids Encoding Embodiments of Antibodies:

In some embodiments, the following nucleic acid sequence was used to encode a neutralizing antibody heavy chain:

(SEQ ID NO: 70)
atggacttcggcctgtcctgggtgttcctggtgctggtgctgaagggcg tgcagtgccaggtgcagctggtggaatccggcggtggcgtggtgcagcc tggcagatccctgagactgtcctgcgccgcctccggcttctccttcgac cggaactactggatcgcctgggtccgacaggcccctggcaagggactgg aatgggtggccgccatctccgctggcggctccggcaacacctactacgc cacctgggccaagggccggttcaccatctcccgggacaactccaagaac accctgtacctgcagatgaactccctgcgggccgaggacaccgccgtgt actactgcgcccggttctacagcggcggaggctactacgccggctactt caccctgtggggccagggcaccctggtcaccgtgtcctccgcctctacc aagggccctccgtgttccctctggccccctccagcaagtccacctctg gcggcaccgccgctctgggctgcctggtcaaggactacttccccgaacc ggtgacggtgtcgtggaactcaggcgccctgaccagcggcgtgcacacc ttcccggctgtcctacagtcctcaggactctactccctcagcagcgtgg tgaccgtgccctccagcagcttgggcacccagacctacatctgcaacgt gaatcacaagcccagcaacaccaaggtggacaagaaagttgagcccaaa tcttgtgacaagactcacacatgcccaccgtgcccagcacctgaactcc tgggggacgtcagtcttcctcttccccccaaaacccaaggacaccct catgatctcccggacccctgaggtcacatgcgtggtggtggacgtgagc cacgaagaccctgaggtcaagttcaactggtacgtggacggcgtggagg tgcataatgccaagacaaagccgcgggaggagcagtacaacagcacgta ccgtgtggtcagcgtcctcaccgtcctgcaccaggactggctgaatggc aaggagtacaagtgcaaggtctccaacaaagccctcccagccccatcg agaaaccatctccaaagccaagggcagccccgagaaccacaggtgta caccctgcccccatcccgggatgagctgaccaagaaccaggtcagcctg acctgcctggtcaaaggcttctatcccagcgacatcgccgtggagtggg agagcaatgggcagccggagaacaactacaagaccacgcctcccgtgtt ggactccgacggctccttcttcctctacagcaagctcaccgtggacaag agcaggtggcagcaggggaacgtcttctcatgctccgtgatgcatgagg ctctgcacaaccactacacgcagaagagcctctccctgtctcccggttga In some embodiments, the following nucleic acid sequence was used to encode a neutralizing antibody light chain:

(SEQ ID NO: 71)
atgagggtccccgctcagctcctggggctccttctgctctggctccctg gagccagatgtgccttccagctgacccagtcccccagctccctgtctgc ctccgtgggcgacagagtgaccatcaactgtcaggcctcccagtccatc ggcggcaacctggcctggtatcagcagaagcccggcaaggcccccaagc tgctgatctacctggcctcctacctggccagcggcgtgccctccagatt ctccggctctggctccggcacccagtttaccctgaccgtgtccagcctg cagcccgaggacttcgccacctactactgccagtcctcctactactccc ccaacgacaacgccttcggccagggcaccaaggtggaaatcaagcgtac ggtggctgcaccatctgtcttcatcttcccgccatctgatgagcagttg aaatctggaactgcctctgttgtgtgcctgctgaataacttctatccca gagaggccaaagtacagtggaaggtggataacgccctccaatcgggtaa ctcccaggagagtgtcacagagcaggacagcaaggacagcacctacagc ctcagcagcaccctgacgctgagcaaagcagactacgagaaacacaaag tctacgcctgcgaagtcacccatcagggcctgagctcgcccgtcacaaa gagcttcaacaggggagagtgttag.

Cell Lines Useful for Expressing the Antibodies:

In some embodiments, one or more neutralizing antibodies can be express in CHO or HEK293 cells. However, any suitable cell line may be used as aspects of the invention are not limited in this respect.

Administration Routes:

In some embodiments, the invention provides methods of inhibiting viral replication, the methods comprising contacting a cell comprising a JC Virus with an antibody composition.

In certain embodiments, an antibody or antibody preparation is administered intravenously. In other embodiments, an antibody or antibody preparation is administered orally. Alternative routes of administration include sublingual, intramuscular, and transdermal administrations. Accordingly, preparations of the present invention may be given orally, parenterally, topically, or rectally. They are of course given in forms suitable for each administration route.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of an antibody, drug or other material other than directly into the central nervous system, such that it enters the patient's system and, thus, is subject to metabolism and other like processes, for example, subcutaneous administration.

Antibody compositions may be administered to humans and other animals for therapy by any suitable route of administration. Actual dosage levels of neutralizing antibodies may be adjusted to obtain an amount that is effective to achieve the desired therapeutic response for a particular patient, composition, and mode of administration, without being toxic to the patient.

The selected dosage level will depend upon a variety of factors including the activity of the particular antibody, the clearance rate of the antibody, the duration of the treatment, other drugs, compounds and/or materials used in combination with the particular antibody, the age, sex, weight, condition, general health and prior medical history of the patient being treated, and like factors well known in the medical arts.

A physician or veterinarian having ordinary skill in the art can readily determine and prescribe the effective amount of the antibody composition required. For example, the physician or veterinarian could start doses of the antibody compositions at levels lower than that required to achieve the desired therapeutic effect and then gradually increasing the dosage until the desired effect is achieved.

In some embodiments, an antibody composition of the invention is provided to a subject chronically. Chronic treatments include any form of repeated administration for an extended period of time, such as repeated administrations for one or more months, between a month and a year, one or more years, or longer. In some embodiments, a chronic treatment involves administering antibody compositions of the invention repeatedly over the life of the subject. In certain embodiments, chronic treatments involve regular administrations, for example one or more times a day, one or more times a week, or one or more times a month. In general, a suitable dose such as a daily dose of antibody compositions of the invention will be that amount that is the lowest dose effective to produce a therapeutic effect. Such an effective dose will generally depend upon the factors described above. In some embodiments, at least 0.5-1 mg/kg may be used. However, higher or lower amounts may be used. In some embodiments, an effective dose of an antibody described herein may be about 100 mg/kg or more. In some embodiments, 300 to 600 mg/kg may be used.

Neutralizing antibody preparations may be formulated for administration in any convenient way for use in human or veterinary medicine, by analogy with other antibodies. In some embodiments, aspects of the invention also relate to a method of making a medicament for use in treating a subject, e.g., for treating or preventing a JVC infection, or for inhibiting JCV replication or proliferation. Such preparations can be used for prophylactic treatment of a subject at risk for or suspected of having a JCV infection or being at risk for PML (e.g., for treatment of a subject prior to, during, and/or after the subject receives an immunomodulatory therapy). Accordingly, one or more antibody compositions described herein that modulate DNA virus replication or proliferation as described herein may be used for the preparation of a medicament for use in any of the methods of treatment described herein. In some embodiments, the invention provides for the use of one or more antibody compositions of the invention (e.g., identified as inhibiting JCV replication) for the manufacture of a medicament or pharmaceutical for treating a mammal (e.g., a human) having one or more symptoms of, or at risk for, JCV infection, replication and/or proliferation (e.g., one or more symptoms of JCV activity). Accordingly, aspects of the invention relate to the use of one or more antibody compositions described herein for the preparation of a medicament for treating or preventing PML in a subject. Accordingly, the invention also relates to one or more antibody compositions described herein for use as a medicament. The invention also relates to one or more of these antibody compositions for use in methods described herein, for example in methods of inhibiting JCV replication, or of treating or preventing a disease associated with JCV replication or proliferation (e.g., in subjects that are about to be, are being, and/or have been treated with at least one immunomodulatory composition).

Diagnostic Applications and Kits:

In some embodiments, antibodies described herein can be used as detection reagents for in vivo diagnostics, and/or coupled to contrast dye reagents for radiology.

In some embodiments, aspects of the invention include using immobilized or non-immobilized, anti-JCV antibodies (e.g., VP-1 binding antibodies) as detection moieties to assess the presence and/or level of JCV in a sample. Detection assays may include the use of one or more labeled detection moieties (e.g., a VP-1 binding antibody containing or attached to a detectable label). A detectable label is defined as any moiety that can be detected using an assay. The antibodies and functional antibody fragments of the invention can be coupled to specific labeling agents for detecting binding according to standard coupling procedures. A wide variety of detectable labels can be used, such as those that provide direct detection (e.g., a radioactive label, a fluorophore, [e.g. Green Fluorescent Protein (GFP), Red Fluorescent Protein (RFP), etc.], a chromophore, an optical or electron dense label, etc.) or indirect detection (e.g., an enzyme tag such as horseradish peroxidase, etc.). Non-limiting examples of detectable labels that have been attached to or incorporated into antibodies include: enzymes, radiolabels, fluorescent labels, phosphorescent molecules, chemiluminescent molecules, chromophores, luminescent molecules, photoaffinity molecules, and colored particles or ligands such as biotin, etc. In some embodiments, detection methods of the invention may include electrochemiluminescence methods (ECL).

A variety of methods may be used to detect a label, depending on the nature of the label and other assay components. Labels may be directly detected through optical or electron density, radioactive emissions, non-radiative energy transfers, etc. or indirectly detected with antibody conjugates, streptavidin-biotin conjugates, etc. Many additional detectable labels are known in the art, as are methods for their attachment to antibodies.

Labeled antibodies of the invention may be antibodies that are used in vitro, e.g., in an immunoassay such as an ELISA. Such detectably labeled antibodies may be antibodies that have a detectable label incorporated into the antibody or may be antibodies that are linked to a secondary binding ligand and/or to an enzyme (an enzyme tag) that will generate a detectable (e.g., colored) product upon contact with a chromogenic substrate. Examples of suitable enzymes include, but are not limited to, urease, alkaline phosphatase, (horseradish) hydrogen peroxidase or glucose oxidase. Examples of suitable secondary binding ligands include, but are not limited to, biotin and/or avidin and streptavidin compounds. The use of such labels is well known to those of skill in the art and is described, for example, in U.S. Pat. Nos. 3,817,837; 3,850,752; 3,939,350; 3,996,345; 4,277,437; 4,275,149 and 4,366,241; each incorporated herein by reference.

Numerous methods for the attachment or conjugation of an antibody to its detectable label are known in the art. An attachment method may include the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3alpha-6alpha-diphenylglycouril-3 attached to the antibody (see, for example, U.S. Pat. Nos. 4,472,509 and 4,938,948, each incorporated herein by reference). Monoclonal antibodies also can be reacted with an enzyme in the presence of a coupling agent such as glutaraldehyde or periodate. Antibodies may be labeled with fluorescein markers in the presence of these coupling agents or by reaction with an isothiocyanate. In other embodiments, antibodies may be labeled by derivatization, for example, by selectively introducing sulfhydryl groups in the Fc region of the antibody, using reaction conditions that do not alter the antibody recognition site.

Detection of a detectable label in an assay of the invention is also referred to herein as detecting the "signal". Methods for detecting the signal in an immunoassay are well known in the art. In some embodiments, an assay signal can be detected using a multi-well plate reader (e.g., microplate reader) to assess the amount and/or location of a signal. Signal detection can be optical detection or other detection means suitable for detecting a detectable label utilized in the invention.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Antibody and CDR Sequences

Antibodies R399 and R411 were generated by immunization of a rabbit with JCV virus-like particles (VLPs). The VLPs used for immunization contained a L55F mutation on the MAD1 background. The spleen of one of four the rabbits was used for the generation of monoclonal antibodies. The antibodies that were generated were screened for infectivity inhibition including antibodies R117, R322, R399, R411 and R497. The selected antibodies were screened for their ability to bind to mutant VLPs and R399 was selected as a potent inhibitor with broad specificity to known viral mutants. Antibodies R399 and R411 were selected for cloning and humanization. The humanization resulted in 3 light chains and 10 heavy chains for both R399 and R411.

399 Based Sequences

399 V-Light and CDRs (underlined)

399_vl

SEQ ID NO: 1

AFELTQTPASVEAAVGGTVTINCQASQSIGNNLAWYQQKPGQPPKLLIYLASYLASGVSSRFKGSGSGTQFTLTV

SALECADAATYYCQSSYYSPNDNAFGGGTEVVVR

399_vl_CDR1

SEQ ID NO: 2

QASQSIGNNLA

399_vl_CDR2

SEQ ID NO: 3

LASYLAS

399_vl_CDR3

SEQ ID NO: 4

QSSYYSPNDNA

V-light Human Acceptor Framework (CDRs underlined)

huIGKV1-13x02

SEQ ID NO: 5

AIQLTQSPSSLSASVGDRVTITCRASQGISSALAWYQQKPGKAPKLLIYDASSLESGVPSRFSGSGSGTDFTLTI

SSLQPEDFATYYCQQFNSYP----FGQGTKVEIK

399 V-Heavy and CDRs (underlined)

399_vh

SEQ ID NO: 6

[illegible]QSLEESGGDLVKPGASLTLTCTVSGFSFDRNYWICWIRQAPGMGLEWAACISAGGSGNTYYATWAKGRFTISKT SS[illegible]TTVTLQMASLTAADTATYFCARFYSGGGYYAGYFTLWGPGTLVTVSS 399_vh_CDR1

SEQ ID NO: 7

GFSFDRNYWIC

```
399_vh_CDR2
                                                          SEQ ID NO: 8
CISAGGSGNTYYATWAKG

399_vh_CDR3
                                                          SEQ ID NO: 9
FYSGGGYYAGYFTL

V-heavy Human Acceptor Framework (CDRs underlined)

IGHV3-30-3x01
                                                          SEQ ID NO: 10
QVQLVESGGGVVQPGRSLRLSCAASGFTFSS-YAMHWVRQAPGKGLEWVAVISYD-GSNKYYADSVKG

RFTISRDNSKNTLYLQMNSLRAEDTAVYYCAR--------------WGQGTLVTVSS
```

Humanized Designs for 399

Light chain: huIGKV1-13×02 framework // 399 VL CDRs

Heavy chain: IGHV3-30-3×01 framework // 399 VH CDRs

Framework backmutations are in lowercase bold font and highlighted. CDRs, according to Chothia definition, are underlined.

All possible pairs or humanized R399 chains were screened for binding to MAD1 JCV VLPs. All bound with high affinity and the CDR grafted version H0L0 was selected as a candidate. That molecule was assayed for binding to a variety of mutant VLPs and differences in binding affinity were noted on some mutants. Most of the described variants had little to no effect on binding or were detrimental. Some improved binding and in particular, light chain variant N31A had significantly improved binding to the VP1 S269F mutant VLP.

Rabbit antibodies frequently contain disulfide bonds bridging regions of the heavy chain variable region from amino acid cys35 to amino acid cys50 (The numbering cys35 and cys50 relates to the original rabbit sequence. Cys 35 and Cys50 correspond to positions 36 and 51, respectively, in the humanized framework sequences). The cysteines were removed in the CDR grafted version of humanized R399 contributing to loss of affinity to on 269F VLPs. Those substitutions were C35A and C50V respectively. In order to remove the disulfide, the C50A was generated (through generation of V50A on the CDR grafted molecule) and no loss of affinity to 269F VLPs was found. The light chain N31A and the heavy chain V50A versions on the H0L2 background were combined to generate antibody "50/31-A". The antibody 50/31-A has restored binding to 269F VLPs and no significant change in binding to other mutants. However, 50/31-A poorly recognizes S269Y VLPs. Assuming that there was a steric hindrance issue, the heavy chain V50G variant was generated and combining with L2-N31A to provide antibody "50/31-G". The antibody 50/31-G binds to S269F and Y and has no significant change in binding to other mutants.

L0 = CDR graft

SEQ ID NO: 11

AIQLTQSPSSLSASVGDRVTITCQASQSIGNNLAWYQQKPGKAPKLLIYLASYLASGVPSRFSGSGSGTDFTLTI

SSLQPEDFATYYCQSSYYSPNDNAFGQGTKVEIK

L1

SEQ ID NO: 12

AfQLTQSPSSLSASVGDRVTITCQASQSIGNNLAWYQQKPGKAPKLLIYLASYLASGVPSRFSGSGSGTDFTLTI

SSLQPEDFATYYCQSSYYSPNDNAFGQGTKVEIK

L2

SEQ ID NO: 13

AfQLTQSPSSLSASVGDRVTInCQASQSIGNNLAWYQQKPGKAPKLLIYLASYLASGVPSRFSGSGSGTqFTLTv

SSLQPEDFATYYCQSSYYSPNDNAFGQGTKVEIK

L2 N31A

SEQ ID NO: 14

AfQLTQSPSSLSASVGDRVTInCQASQSIGANLAWYQQKPGKAPKLLIYLASYLASGVPSRFSGSGSGTqFTLTv

SSLQPEDFATYYCQSSYYSPNDNAFGQGTKVEIK

L2 N31G

SEQ ID NO: 15

AfQLTQSPSSLSASVGDRVTInCQASQSIGGNLAWYQQKPGKAPKLLIYLASYLASGVPSRFSGSGSGTqFTLTv

SSLQPEDFATYYCQSSYYSPNDNAFGQGTKVEIK

```
399_v1_CDR1 N31A                                              SEQ ID NO: 16
QASQSIGANLA

399_v1_CDR1 N31G                                              SEQ ID NO: 17
QASQSIGGNLA

399_v1_CDR1 N31X                                              SEQ ID NO: 18
QASQSIGXNLA

H0 = CDR graft                                                SEQ ID NO: 19
QVQLVESGGGVVQPGRSLRLSCAASGFSFDRNYWIAWVRQAPGKGLEWVAVISAGGSGNTYYATWAKGRFTISRD
NSKNTLYLQMNSLRAEDTAVYYCARFYSGGGYYAGYFTLWGQGTLVTVSS H0 V50A                                                       SEQ ID NO: 20
QVQLVESGGGVVQPGRSLRLSCAASGFSFDRNYWIAWVRQAPGKGLEWVAAISAGGSGNTYYATWAKGRFTISRD
NSKNTLYLQMNSLRAEDTAVYYCARFYSGGGYYAGYFTLWGQGTLVTVSS H0 V50G                                                       SEQ ID NO: 21
QVQLVESGGGVVQPGRSLRLSCAASGFSFDRNYWIAWVRQAPGKGLEWVAGISAGGSGNTYYATWAKGRFTISRD
NSKNTLYLQMNSLRAEDTAVYYCARFYSGGGYYAGYFTLWGQGTLVTVSS H1                                                            SEQ ID NO: 22
QVQLVQSGGGVVQPGRSLRLSCAVSGFSFDRNYWIAWVRQAPGKGLEWVAVISAGGSGNTYYATWAKGRFTISKD
NSKNTLYLQMNSLRAEDTAVYYCARFYSGGGYYAGYFTLWGQGTLVTVSS H2                                                            SEQ ID NO: 23
QVQLVQSGGGVVQPGESLRLSCAVSGFSFDRNYWIAWIRQAPGKGLEWAAVISAGGSGNTYYATWAKGRFTISKD
NSKNTVYLQMNSLRAEDTAVYFCARFYSGGGYYAGYFTLWGQGTLVTVSS H3                                                            SEQ ID NO: 24
QVQLVQSGGGVVQPGESLRLSCAVSGFSFDRNYWISWIRQAPGKGLEWAAVISAGGSGNTYYATWAKGRFTISKD
NSKNTVYLQMNSLRAEDTAVYFCARFYSGGGYYAGYFTLWGQGTLVTVSS H4                                                            SEQ ID NO: 25
QVQLVQSGGGVVQPGESLRLSCAVSGFSFDRNYWICWIRQAPGKGLEWAACISAGGSGNTYYATWAKGRFTISKD
NSKNTVYLQMNSLRAEDTAVYFCARFYSGGGYYAGYFTLWGQGTLVTVSS H5                                                            SEQ ID NO: 26
Q-QLVQSGGGVVQPGESLRLSCAVSGFSFDRNYWIAWIRQAPGKGLEWAAVISAGGSGNTYYATWAKGRFTISKD
NSKNTVYLQMNSLRAEDTAVYFCARFYSGGGYYAGYFTLWGQGTLVTVSS H6                                                            SEQ ID NO: 27
QVQLVQSGGGVVQPGESLRLSCAVSGFSFDRNYWIAWIRQAPGKGLEWAAVISAGGSGNTYYATWAKGRFTISKT
SSSTVYLQMNSLRAEDTAVYFCARFYSGGGYYAGYFTLWGQGTLVTVSS H7                                                            SEQ ID NO: 28
Q-QLVQSGGGVVQPGESLRLSCAVSGFSFDRNYWIAWIRQAPGKGLEWAAVISAGGSGNTYYATWAKGRFTISKT
SSSTVYLQMNSLRAEDTAVYFCARFYSGGGYYAGYFTLWGQGTLVTVSS

H8
```

-continued

SEQ ID NO: 29
Q_QLV_SGGGVVQPG_SLRLSCA_SGFSFDRNYWI_W_RQAPGKGLEW_A_ISAGGSGNTYYATWAKGRFTIS__

_S__T_YLQMNSLRAEDTAVY_CARFYSGGGYYAGYFTLWGQGTLVTVSS

H9

SEQ ID NO: 30
Q_QLV_SGGGVVQPG_SLRLSCA_SGFSFDRNYWI_W_RQAPGKGLEW_A_ISAGGSGNTYYATWAKGRFTIS__

_S__T_YLQMNSLRAEDTAVY_CARFYSGGGYYAGYFTLWGQGTLVTVSS

399_vh_CDR1 C35A

SEQ ID NO: 31
GFSFDRNYWIA

399_vh_CDR1 C35S

SEQ ID NO: 32
GFSFDRNYWIS

399_vh_CDR1 C35X

SEQ ID NO: 33
GFSFDRNYWIX

399_vh_CDR2 C50V

SEQ ID NO: 34
VISAGGSGNTYYATWAKG

399_vh_CDR2 C50A

SEQ ID NO: 35
AISAGGSGNTYYATWAKG

399_vh_CDR2 C50G

SEQ ID NO: 36
GISAGGSGNTYYATWAKG

399_vh_CDR2 C50X

SEQ ID NO: 37
XISAGGSGNTYYATWAKG

Mutations in Reshaped VL

| L0 to L1 | |
|---|---|
| I2F | This canonical residue could affect the conformation of CDR L1. |
| L1 to L2 | |
| T22N | This residue is surface exposed near CDR L1 and may contact antigen. |
| D70Q | This residue is surface exposed near CDR L1 and may contact antigen. |
| I75V | This residue is buried in the core and may affect the structure of the VL domain. |

The Position can be Translated into Kabat Numbering
Mutations in Reshaped VH

| H0 to H1 | |
|---|---|
| E6Q | This buried mutation has improved VH domain stability in other antibodies. |
| A24V | This canonical residue may affect the conformation of CDR H1. |
| R71K | This canonical residue may affect the conformation of CDR H2. |
| H1 to H2 | |
| R16E | This mutation has improved VH domain stability in several other antibodies. |
| V37I | This residue is located at the VH/VL domain interface and may affect heavy/light chain pairing. |
| V48A | This buried residue may affect the structure of CDR H2. |
| L78V | This buried residue may affect the structure of CDR H1. |
| Y91F | This residue is located at the VH/VL domain interface and may affect heavy/light chain pairing. |

Constructs H3-H9

There are several unusual characteristics of rabbit VH domains that are not observed in human VH domains. These characteristics include:

Shortened N-terminus. In this rabbit VH domain, framework 1 is shorter by one residue than in the typical human VH domain. Instead of a backmutation, some humanized constructs were made more like rabbit 399 by deleting Val2. V2Δ mutants are highlighted in the constructs above.

Shortened framework 3. In this rabbit VH domain, framework 3 is also shorter by one residue than framework 3 in most known human VH domains. Since the loop region of framework 3 near CDR 1 can sometimes recognize antigen, this region of some humanized constructs was shortened and replaced with the rabbit sequence. The combined mutations/deletion (D72T/N73S/K75Δ/N76T) was used to make this region of the VH domain more like rabbit 399. Shortened framework 3 regions are highlighted in the constructs above.

Disulfide bond between Cys35a and Cys50. This disulfide bond does not occur in human VH domains. The residues Cys35a and Cys50 were replaced with Ser/Ala and Val, respectively, in some constructs. These amino acids are highlighted in the sequences above.

| Construct | Shortened N-terminus? | Shortened framework 3? | Residues 35a and 50 |
|---|---|---|---|
| H2 | No | No | Ala, Val |
| H3 | No | No | Ser, Val |
| H4 | No | No | Cys, Cys |
| H5 | Yes | No | Ala, Val |
| H6 | No | Yes | Ala, Val |
| H7 | Yes | Yes | Ala, Val |
| H8 | Yes | Yes | Ser, Val |
| H9 | Yes | Yes | Cys, Cys |

411-Based Sequences

411 V-Light and CDRs jcv411_vl
SEQ ID NO: 38

AFELTQTTSPVSAAVGGTVTIFC<u>QASQSIGNNLA</u>WYQQKPGQPPKLLIY

<u>LASYLAS</u>GVPSRFKGSGSGTQFTLTVSALECADAAAYYC<u>QSAYYSPNDN</u>

<u>A</u>FGGGTEVVVR

Human Acceptor Framework

IGKV1D-13x01
SEQ ID NO: 39

AIQLTQSPSSLSASVGDRVTITC<u>QASQSIGNNLA</u>WYQQKPGKAPKLLIY

<u>LASYLAS</u>GVPSRFSGSGSGTDFTLTISSLQPEDFATYYC<u>QSAYYSPNDN</u>

<u>A</u>FGQGTKVEIK jcv411_vl_CDR1
SEQ ID NO: 40

QASQSIGNNLA jcv411_vl_CDR2
SEQ ID NO: 41

LASYLAS jcv411_vl_CDR3
SEQ ID NO: 42

QSAYYSPNDNA

411 V-Heavy and CDRs jcv411_vh
SEQ ID NO: 43

Q*SLEESGGDLVKPGASLTLTCTAS<u>GFSFDRNYWM</u>*WVRQAPGMGLEWAA<u>*IAAGGNGNTYYATWAKG</u>RFTISKT

SST*TVTLQMASLTAADTATYFCAR<u>FYNGGGYYAGYFTL</u>WGPGTLVTVSS

IGHV3-30-3x01
SEQ ID NO: 44

QVQLVESGGGVVQPGRSLRLSCAAS<u>GFTFSS-YAMH</u>WVRQAPGKGLEWVA<u>VISYD-GSNKYYADSVKG</u>RFTISR

DNSKNTLYLQMNSLRAEDTAVYYCAR--------------WGQGTLVTVSS

Human Acceptor Framework jcv411_vh_CDR1
SEQ ID NO: 45

GFSFDRNYWMC jcv411_vh_CDR2
SEQ ID NO: 46

CIAAGGNGNTYYATWAKG jcv411_vh_CDR3
SEQ ID NO: 47

FYNGGGYYAGYFTL

Humanization Designs for 411

Light chain: IGKV1D-13×01 framework II jcv411_vl CDRs

Heavy chain: IGHV3-30-3×01 framework II jcv411_vh CDRs

Framework backmutations are in lowercase bold font and highlighted. CDRs, according to Chothia definition, are underlined.

```
L0 = CDR graft
                                                       SEQ ID NO: 48
AIQLTQSPSSLSASVGDRVTITCQASQSIGNNLAWYQQKPGKAPKLLIYLASYLASGVPSRFSGSGSGTDFTLTI

SSLQPEDFATYYCQSAYYSPNDNAFGQGTKVEIK

L1
                                                       SEQ ID NO: 49
AiQLTQSPSSLSASVGDRVTITCQASQSIGNNLAWYQQKPGKAPKLLIYLASYLASGVPSRFSGSGSGTDFTLTI

SSLQPEDFATYYCQSAYYSPNDNAFGQGTKVEIK

L2
                                                       SEQ ID NO: 50
AiQLTQSPSSLSASVGDRVTIsCQASQSIGNNLAWYQQKPGKAPKLLIYLASYLASGVPSRFSGSGSGTdFTLTv

SSLQPEDFATYYCQSAYYSPNDNAFGQGTKVEIK

H0 = CDR graft
                                                       SEQ ID NO: 51
QVQLVESGGGVVQPGRSLRLSCAASGFSFDRNYWMAWVRQAPGKGLEWVAVIAAGGSGNTYYATWAKGRFTISRD

NSKNTLYLQMNSLRAEDTAVYYCARFYSGGGYYAGYFTLWGQGTLVTVSS

H1
                                                       SEQ ID NO: 52
QVQLVqSGGGVVQPGRSLRLSCAASGFSFDRNYWMAWVRQAPGKGLEWVAVIAAGGSGNTYYATWAKGRFTISkD

NSKNTLYLQMNSLRAEDTAVYYCARFYSGGGYYAGYFTLWGQGTLVTVSS

H2
                                                       SEQ ID NO: 53
QVQLVqSGGGVVQPGkSLRLSCAASGFSFDRNYWMAWVRQAPGKGLEWaAVIAAGGSGNTYYATWAKGRFTISkD

NSKNTvYLQMNSLRAEDTAVYfCARFYSGGGYYAGYFTLWGQGTLVTVSS

H3
                                                       SEQ ID NO: 54
QVQLVqSGGGVVQPGkSLRLSCAASGFSFDRNYWMsWVRQAPGKGLEWaAVIAAGGSGNTYYATWAKGRFTISkD

NSKNTvYLQMNSLRAEDTAVYfCARFYSGGGYYAGYFTLWGQGTLVTVSS

H4
                                                       SEQ ID NO: 55
QVQLVqSGGGVVQPGkSLRLSCAASGFSFDRNYWMgWVRQAPGKGLEWaAgIAAGGSGNTYYATWAKGRFTISkD

NSKNTvYLQMNSLRAEDTAVYfCARFYSGGGYYAGYFTLWGQGTLVTVSS

H5
                                                       SEQ ID NO: 56
QiQLVqSGGGVVQPGkSLRLSCAASGFSFDRNYWMAWVRQAPGKGLEWaAVIAAGGSGNTYYATWAKGRFTISkD

NSKNTvYLQMNSLRAEDTAVYfCARFYSGGGYYAGYFTLWGQGTLVTVSS

H6
```

-continued

```
                                                                  SEQ ID NO: 57
QVQLVQSGGGVVQPGXSLRLSCAASGFSFDRNYWMAWVRQAPGKGLEWXAVIAAGGSGNTYYATWAKGRFTISXX

XXXXTXYLQMNSLRAEDTAVYXCARFYSGGGYYAGYFTLWGQGTLVTVSS

H7
                                                                  SEQ ID NO: 58
QXQLVQSGGGVVQPGXSLRLSCAASGFSFDRNYWMAWVRQAPGKGLEWXAVIAAGGSGNTYYATWAKGRFTISXX

XXXXTXYLQMNSLRAEDTAVYXCARFYSGGGYYAGYFTLWGQGTLVTVSS

H8
                                                                  SEQ ID NO: 59
QXQLVQSGGGVVQPGXSLRLSCAASGFSFDRNYWMXWVRQAPGKGLEWXAVIAAGGSGNTYYATWAKGRFTISXX

XXXXTXYLQMNSLRAEDTAVYXCARFYSGGGYYAGYFTLWGQGTLVTVSS

H9
                                                                  SEQ ID NO: 60
QXQLVCSGGGVVQPGXSLRLSCAASGFSFDRNYWMXWVRQAPGKGLEWXAXIAAGGSGNTYYATWAKGRFTISXX

XXXXTXYLQMNSLRAEDTAVYXCARFYSGGGYYAGYFTLWGQGTLVTVSS jcv411_vh_CDR1 C35A
                                                                  SEQ ID NO: 61
GFSFDRNYWMA jcv411_vh_CDR1 C35S
                                                                  SEQ ID NO: 62
GFSFDRNYWMS jcv411_vh_CDR1 C35X
                                                                  SEQ ID NO: 63
GFSFDRNYWMX jcv411_vh_CDR2 C50V
                                                                  SEQ ID NO: 64
VIAAGGSGNTYYATWAKG jcv411_vh_CDR2 C50X
                                                                  SEQ ID NO: 65
XIAAGGSGNTYYATWAKG
```

Mutations in Reshaped VL

| L0 to L1 | |
|---|---|
| I2F | This canonical residue could affect the conformation of CDR L1. |
| L1 to L2 | |
| T22F | This residue is surface exposed near CDR L1 and may contact antigen. |
| D70Q | This residue is surface exposed near CDR L1 and may contact antigen. |
| I75V | This residue is buried in the core and may affect the structure of the VL domain. |

Mutations in Reshaped VH

| H0 to H1 | |
|---|---|
| E6Q | This buried mutation has improved VH domain stability in other antibodies. |
| R71K | This canonical residue may affect the conformation of CDR H2. |
| H1 to H2 | |
| R16E | This mutation has improved VH domain stability in several other antibodies. |
| V48A | This buried residue may affect the structure of CDR H2. |
| L78V | This buried residue may affect the structure of CDR H1. |

| | |
|---|---|
| Y91F | This residue is located at the VH/VL domain interface and may affect heavy/light chain pairing. |

Constructs H3-H9

There are several unusual characteristics of rabbit VH domains that are not observed in human VH domains. These characteristics include:

- Shortened N-terminus. In this rabbit VH domain, framework 1 is shorter by one residue than in the typical human VH domain. Instead of a backmutation, some humanized constructs were made more like rabbit 399 by deleting Val2. V2Δ mutants are highlighted in the constructs above.
- Shortened framework 3. In this rabbit VH domain, framework 3 is also shorter by one residue than framework 3 in most known human VH domains. Since the loop region of framework 3 near CDR 1 can sometimes recognize antigen, this region of some humanized constructs was shortened and replaced with the rabbit sequence. The combined mutations/deletion (D72T/N73S/K75Δ/N76T) was used to make this region of the VH domain more like rabbit 399. Shortened framework 3 regions are highlighted in the constructs above.
- Disulfide bond between Cys35a and Cys50. This disulfide bond does not occur in human VH domains. The residues Cys35a and Cys50 were replaced with Ser/Ala and Val, respectively, in some constructs. These amino acids are highlighted in the sequences above.

| Construct | Shortened N-terminus? | Shortened framework 3? | Residues 35a and 50 |
|---|---|---|---|
| H2 | No | No | Ala, Val |
| H3 | No | No | Ser, Val |
| H4 | No | No | Cys, Cys |
| H5 | Yes | No | Ala, Val |
| H6 | No | Yes | Ala, Val |
| H7 | Yes | Yes | Ala, Val |
| H8 | Yes | Yes | Ser, Val |
| H9 | Yes | Yes | Cys, Cys |

Example 2

Neutralization Assay

Figure 2:
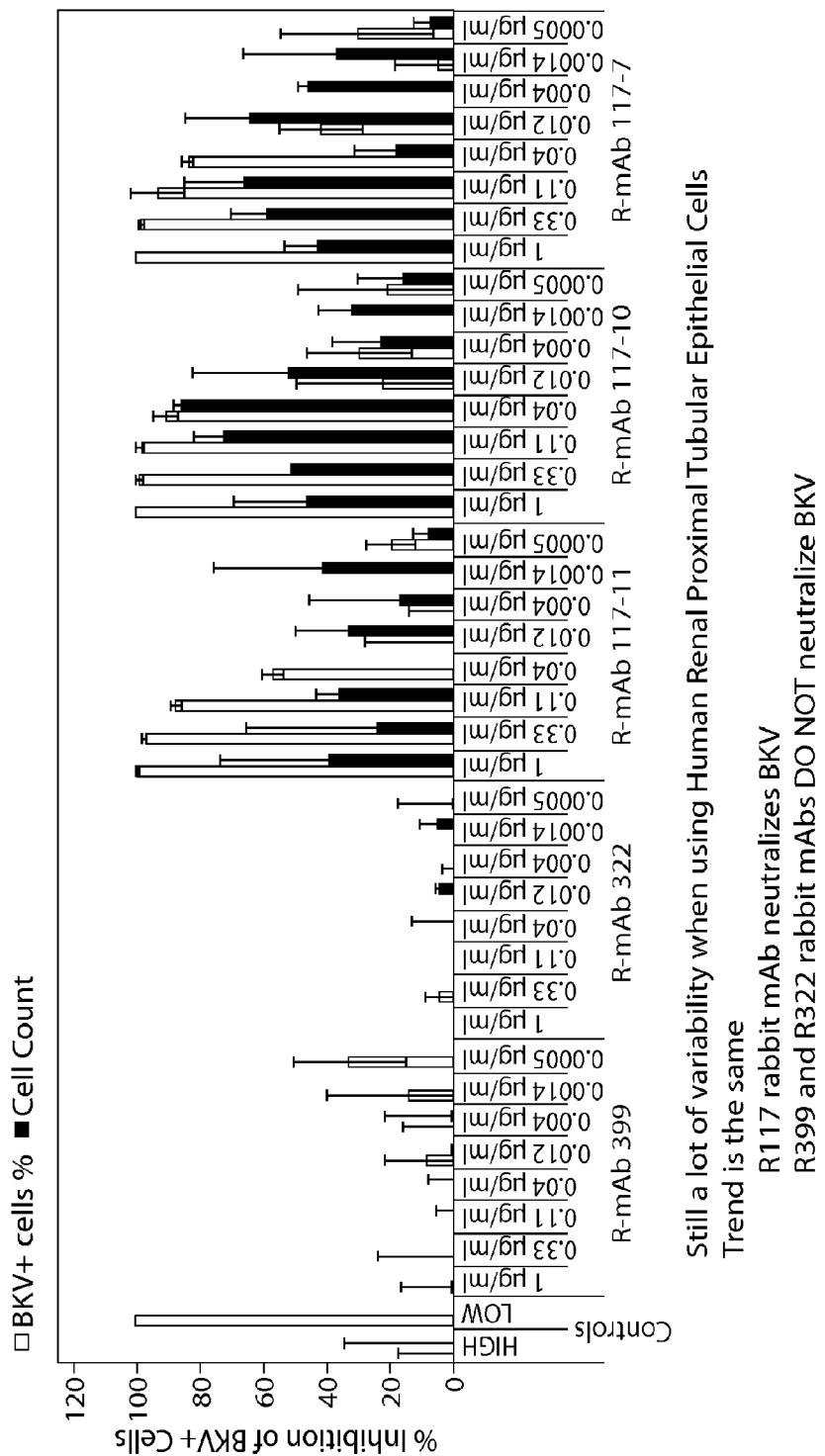
FIG. 2 shows the results of the ability of rabbit-derived monoclonal antibodies to neutralize JCV and BKV virus in a human renal proximal tubular epithelial infectivity inhibition assay.

Rabbit-derived monoclonal antibodies were tested in a human astrocytes doubling assay for their ability to neutralize JCV and BKV virus. The ability of the antibodies to inhibit the virus and cells is shown in FIG. 1 (human astrocytes) and FIG. 2 (human renal proximal tubular epithelial cells). FIG. 3 provides an overview of the EC50, EC80 and EC90 of the antibodies against JCV and BKV in the various assays.

Example 3

Binding to JCV-VP1 of Rabbit-Derived Monoclonal Antibodies

Rabbit-derived monoclonal antibodies were tested for their ability to bind the JCV-VP1 wild-type protein and the following JCV-VP1 mutants; L55F, S269F, Q271H, K60E and D66H. The binding studies were performed in an ELISA assay. The results are shown in FIG. 4.

Example 4

Binding to JCV-VP1 of Humanized Versions of 399 Rabbit-Derived Monoclonal Antibodies as Determined by ELISA The CDRs of the rabbit-derived monoclonal antibody 399 were grafted into humanized V-heavy and V-light acceptor sequences as described in Example 1. The binding of the rabbit-monoclonal 399 and the humanized antibodies BIIB048 (=H0L0), $H0_{V50A} L2_{N31A}$ and $H0_{V50A} L2_{N31A}$ to a number of wild-type and mutant JCV-VP1 was evaluated using ELISA. The results are summarized in FIG. 5.

Example 5

Binding to JCV-VP1 of Humanized Versions of 399 Rabbit-Derived Monoclonal Antibodies as Determined by Biacore Affinity Experiments The CDRs of the rabbit-derived monoclonal antibody 399 were grafted into humanized V-heavy and V-light acceptor sequences as described in Example 1. The binding of the humanized antibodies BIIB048 (=H0L0) and $H0_{V50A} L2_{N31A}$ to a number of wild-type and mutant JCV-VP1 was evaluated using Biacore affinity experiments. The binding of both the Fab and Mab versions of the antibodies was determined. The results are summarized in FIG. 6.

Example 6

Infectivity Assay

Figure 8:
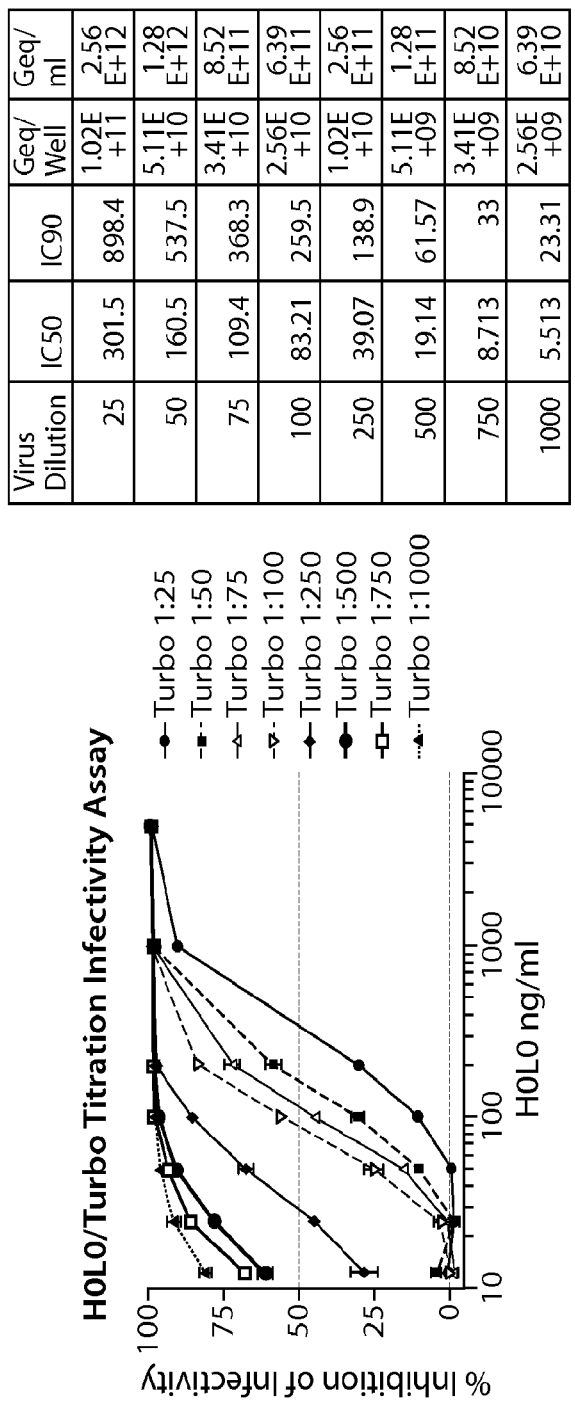
FIG. 8 shows the ability of antibody H0L0 to suppress the infectivity of JCV.

The ability of antibody H0L0 to suppress the infectivity of the JCV was evaluated at various virus concentration and the $IC_{50}$ and $IC_{90}$ of the antibody determined. The results are shown in FIG. 8.

Example 7

Infectivity Assay with Mutant JCV-VP1 Viruses

The ability of antibodies BIIB48 (H0L0) and hu399 50-31G ($H0_{V50A} L2_{N31A}$) to suppress the infectivity of the JCV-VP1 mutants was evaluated. The assay conditions are provided on FIG. 9 and FIG. 10. The read-out of the experiments was done by Western-Blots. The results of the Western blots are shown in FIGS. 11-12 (regular exposure) and FIGS. 13-14 (over-exposure).

Example 8

Binding of Humanized Antibodies to Mutant JCV-VP1 Viruses

The ability of antibodies BIIB48 (H0L0) and hu399 50-31G ($H0_{V50A} L2_{N31A}$) to bind the various JCV-VP1 mutants was evaluated by ELISA. The assay conditions are provided in FIG. 15 and FIG. 16. The $EC_{50}$ values (in nM) are provided in FIG. 17.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims.

The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. An isolated monoclonal antibody comprising:
   a heavy chain variable domain comprising a CDR1 amino acid sequence that is identical to the amino acid sequence of SEQ ID NO:31, a CDR2 amino acid sequence that is identical to the amino acid sequence of SEQ ID NO:35, and a CDR3 amino acid sequence that is identical to the amino acid sequence of SEQ ID NO:9; and
   a light chain variable domain comprising a CDR1 amino acid sequence that is identical to the amino acid sequence of SEQ ID NO:17, a CDR2 amino acid sequence that is identical to the amino acid sequence of SEQ ID NO:3, and a CDR3 amino acid sequence that is identical to the amino acid sequence of SEQ ID NO:4.

2. The isolated monoclonal antibody of claim 1, wherein at least one framework region amino acid sequence of the heavy chain variable domain is at least 90% identical to at least one corresponding framework region amino acid sequence of a heavy chain variable domain amino acid sequence that is identical to the amino acid sequence of SEQ ID NO:20.

3. The isolated monoclonal antibody of claim 1, wherein the isolated monoclonal antibody comprises a heavy chain variable domain amino acid sequence that is at least 90% identical to the amino acid sequence of SEQ ID NO:20.

4. The isolated monoclonal antibody of claim 3, wherein the isolated monoclonal antibody comprises a heavy chain variable domain amino acid sequence that is identical to the amino acid sequence of SEQ ID NO:20.

5. The isolated monoclonal antibody of claim 1, wherein at least one framework region amino acid sequence of the light chain variable domain is at least 90% identical to at least one corresponding framework region amino acid sequence of a light chain variable domain amino acid sequence that is identical to the amino acid sequence of SEQ ID NO:15.

6. The isolated monoclonal antibody of claim 1, wherein the isolated monoclonal antibody comprises a light chain variable domain amino acid sequence that is at least 90% identical to the amino acid sequence of SEQ ID NO:15.

7. The isolated monoclonal antibody of claim 6, wherein the isolated monoclonal antibody comprises a light chain variable domain amino acid sequence that is identical to the amino acid sequence of SEQ ID NO:15.

8. The isolated monoclonal antibody of claim 1, wherein the isolated monoclonal antibody comprises a heavy chain variable domain amino acid sequence that is identical to the amino acid sequence of SEQ ID NO:20 and a light chain variable domain amino acid sequence that is identical to the amino acid sequence of SEQ ID NO:15.

9. The isolated monoclonal antibody of claim 1, wherein the isolated monoclonal antibody is an isolated chimeric monoclonal antibody.

10. The isolated monoclonal antibody of claim 1, wherein the isolated monoclonal antibody comprises an IgG1 Fc-region.

11. The isolated monoclonal antibody of claim 8, wherein the isolated monoclonal antibody is an isolated chimeric monoclonal antibody.

12. The isolated monoclonal antibody of claim 8, wherein the isolated monoclonal antibody comprises an IgG1 Fc-region.

* * * * *

SEQUENCE LISTING

```
<160> NUMBER OF SEQ ID NOS: 71

<210> SEQ ID NO 1
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 1

Ala Phe Glu Leu Thr Gln Thr Pro Ala Ser Val Glu Ala Ala Val Gly
1               5                   10                  15

Gly Thr Val Thr Ile Asn Cys Gln Ala Ser Gln Ser Ile Gly Asn Asn
            20                  25                  30

Leu Ala Trp Tyr Gln Gln Lys Pro Gly Gln Pro Pro Lys Leu Leu Ile
        35                  40                  45

Tyr Leu Ala Ser Tyr Leu Ala Ser Gly Val Ser Ser Arg Phe Lys Gly
    50                  55                  60

Ser Gly Ser Gly Thr Gln Phe Thr Leu Thr Val Ser Ala Leu Glu Cys
65                  70                  75                  80

Ala Asp Ala Ala Thr Tyr Tyr Cys Gln Ser Ser Tyr Tyr Ser Pro Asn
                85                  90                  95

Asp Asn Ala Phe Gly Gly Gly Thr Glu Val Val Val Arg
            100                 105

<210> SEQ ID NO 2
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 2

Gln Ala Ser Gln Ser Ile Gly Asn Asn Leu Ala
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 3

Leu Ala Ser Tyr Leu Ala Ser
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 4

Gln Ser Ser Tyr Tyr Ser Pro Asn Asp Asn Ala
1               5                   10
```

```
<210> SEQ ID NO 5
<211> LENGTH: 109
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (96)..(99)
<223> OTHER INFORMATION: Xaa can be any naturally occurring amino acid

<400> SEQUENCE: 5

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Xaa
                85                  90                  95

Xaa Xaa Xaa Phe Gly Gln Gly Thr Lys Val Glu Ile Lys
            100                 105

<210> SEQ ID NO 6
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 6

Xaa Gln Ser Leu Glu Glu Ser Gly Gly Asp Leu Val Lys Pro Gly Ala
1               5                   10                  15

Ser Leu Thr Leu Thr Cys Thr Val Ser Gly Phe Ser Phe Asp Arg Asn
            20                  25                  30

Tyr Trp Ile Cys Trp Ile Arg Gln Ala Pro Gly Met Gly Leu Glu Trp
        35                  40                  45

Ala Ala Cys Ile Ser Ala Gly Gly Ser Gly Asn Thr Tyr Tyr Ala Thr
50                  55                  60

Trp Ala Lys Gly Arg Phe Thr Ile Ser Lys Thr Ser Ser Xaa Thr Thr
65                  70                  75                  80

Val Thr Leu Gln Met Ala Ser Leu Thr Ala Ala Asp Thr Ala Thr Tyr
                85                  90                  95

Phe Cys Ala Arg Phe Tyr Ser Gly Gly Gly Tyr Tyr Ala Gly Tyr Phe
            100                 105                 110

Thr Leu Trp Gly Pro Gly Thr Leu Val Thr Val Ser Ser
        115                 120                 125
```

-continued

```
<210> SEQ ID NO 7
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 7

Gly Phe Ser Phe Asp Arg Asn Tyr Trp Ile Cys
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 8

Cys Ile Ser Ala Gly Gly Ser Gly Asn Thr Tyr Tyr Ala Thr Trp Ala
1               5                   10                  15

Lys Gly

<210> SEQ ID NO 9
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 9

Phe Tyr Ser Gly Gly Gly Tyr Tyr Ala Gly Tyr Phe Thr Leu
1               5                   10

<210> SEQ ID NO 10
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (101)..(114)
<223> OTHER INFORMATION: Xaa can be any naturally occurring amino acid

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Xaa
                20                  25                  30

Tyr Ala Met His Trp Val Arg Gln Ala Pro Gly Lys Gly Leu Glu Trp
            35                  40                  45

Val Ala Val Ile Ser Tyr Asp Xaa Gly Ser Asn Lys Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Ala Arg Xaa Xaa Xaa Xaa Xaa Xaa Xaa Xaa Xaa Xaa
                100                 105                 110

Xaa Xaa Trp Gly Gln Gly Thr Leu Val Thr Val Ser Ser
        115                 120                 125

<210> SEQ ID NO 11
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 11

Ala Ile Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Gly Asn Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Tyr Ser Pro Asn
                85                  90                  95

Asp Asn Ala Phe Gly Gln Gly Thr Lys Val Glu Ile Lys
            100                 105

<210> SEQ ID NO 12
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 12

Ala Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Gly Asn Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Tyr Ser Pro Asn
                85                  90                  95

Asp Asn Ala Phe Gly Gln Gly Thr Lys Val Glu Ile Lys
            100                 105

<210> SEQ ID NO 13
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 13
```

```
Ala Phe Gln Leu Thr Gln Ser Pro Ser Ser Leu Ser Ala Ser Val Gly
1               5                   10                  15

Asp Arg Val Thr Ile Asn Cys Gln Ala Ser Gln Ser Ile Gly Asn Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Gln Phe Thr Leu Thr Val Ser Ser Leu Gln Pro
65                  70                  75                  80

Glu Asp Phe Ala Thr Tyr Tyr Cys Gln Ser Ser Tyr Tyr Ser Pro Asn
                85                  90                  95

Asp Asn Ala Phe Gly Gln Gly Thr Lys Val Glu Ile Lys
            100                 105
```

<210> SEQ ID NO 14
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 14

```
Ala Phe Gln Leu Thr Gln Ser Pro Ser Ser Leu Ser Ala Ser Val Gly
1               5                   10                  15

Asp Arg Val Thr Ile Asn Cys Gln Ala Ser Gln Ser Ile Gly Ala Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Gln Phe Thr Leu Thr Val Ser Ser Leu Gln Pro
65                  70                  75                  80

Glu Asp Phe Ala Thr Tyr Tyr Cys Gln Ser Ser Tyr Tyr Ser Pro Asn
                85                  90                  95

Asp Asn Ala Phe Gly Gln Gly Thr Lys Val Glu Ile Lys
            100                 105
```

<210> SEQ ID NO 15
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 15

```
Ala Phe Gln Leu Thr Gln Ser Pro Ser Ser Leu Ser Ala Ser Val Gly
1               5                   10                  15

Asp Arg Val Thr Ile Asn Cys Gln Ala Ser Gln Ser Ile Gly Gly Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Gln Phe Thr Leu Thr Val Ser Ser Leu Gln Pro
65                  70                  75                  80

Glu Asp Phe Ala Thr Tyr Tyr Cys Gln Ser Ser Tyr Tyr Ser Pro Asn
                85                  90                  95
```

```
Asp Asn Ala Phe Gly Gln Gly Thr Lys Val Glu Ile Lys
            100                 105

<210> SEQ ID NO 16
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 16

Gln Ala Ser Gln Ser Ile Gly Ala Asn Leu Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 17

Gln Ala Ser Gln Ser Ile Gly Gly Asn Leu Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 18

Gln Ala Ser Gln Ser Ile Gly Xaa Asn Leu Ala
1               5                   10

<210> SEQ ID NO 19
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Asp Arg Asn
            20                  25                  30

Tyr Trp Ile Ala Trp Val Arg Gln Ala Pro Gly Lys Gly Leu Glu Trp
        35                  40                  45

Val Ala Val Ile Ser Ala Gly Gly Ser Gly Asn Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Phe Tyr Ser Gly Gly Tyr Tyr Ala Gly Tyr Phe
            100                 105                 110

Thr Leu Trp Gly Gln Gly Thr Leu Val Thr Val Ser Ser
```

-continued

```
                115                 120                 125

<210> SEQ ID NO 20
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Asp Arg Asn
            20                  25                  30

Tyr Trp Ile Ala Trp Val Arg Gln Ala Pro Gly Lys Gly Leu Glu Trp
        35                  40                  45

Val Ala Ala Ile Ser Ala Gly Gly Ser Gly Asn Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
        115                 120                 125

<210> SEQ ID NO 21
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Asp Arg Asn
            20                  25                  30

Tyr Trp Ile Ala Trp Val Arg Gln Ala Pro Gly Lys Gly Leu Glu Trp
        35                  40                  45

Val Ala Gly Ile Ser Ala Gly Gly Ser Gly Asn Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
        115                 120                 125

<210> SEQ ID NO 22
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 22
```

Gln Val Gln Leu Val Gln Ser Gly Gly Gly Val Val Gln Pro Gly Arg
1               5                   10                  15

Ser Leu Arg Leu Ser Cys Ala Val Ser Gly Phe Ser Phe Asp Arg Asn
            20                  25                  30

Tyr Trp Ile Ala Trp Val Arg Gln Ala Pro Gly Lys Gly Leu Glu Trp
        35                  40                  45

Val Ala Val Ile Ser Ala Gly Gly Ser Gly Asn Thr Tyr Tyr Ala Thr
    50                  55                  60

Trp Ala Lys Gly Arg Phe Thr Ile Ser Lys Asp Asn Ser Lys Asn Thr
65              70                  75                  80

Leu Tyr Leu Gln Met Asn Ser Leu Arg Ala Glu Asp Thr Ala Val Tyr
                85                  90                  95

Tyr Cys Ala Arg Phe Tyr Ser Gly Gly Tyr Tyr Ala Gly Tyr Phe
                100                 105                 110

Thr Leu Trp Gly Gln Gly Thr Leu Val Thr Val Ser Ser
        115                 120                 125

<210> SEQ ID NO 23
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 23

Gln Val Gln Leu Val Gln Ser Gly Gly Gly Val Val Gln Pro Gly Glu
1               5                   10                  15

Ser Leu Arg Leu Ser Cys Ala Val Ser Gly Phe Ser Phe Asp Arg Asn
            20                  25                  30

Tyr Trp Ile Ala Trp Ile Arg Gln Ala Pro Gly Lys Gly Leu Glu Trp
        35                  40                  45

Ala Ala Val Ile Ser Ala Gly Gly Ser Gly Asn Thr Tyr Tyr Ala Thr
    50                  55                  60

Trp Ala Lys Gly Arg Phe Thr Ile Ser Lys Asp Asn Ser Lys Asn Thr
65              70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Tyr Tyr Ala Gly Tyr Phe
                100                 105                 110

Thr Leu Trp Gly Gln Gly Thr Leu Val Thr Val Ser Ser
        115                 120                 125

<210> SEQ ID NO 24
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 24

Gln Val Gln Leu Val Gln Ser Gly Gly Gly Val Val Gln Pro Gly Glu
1               5                   10                  15

Ser Leu Arg Leu Ser Cys Ala Val Ser Gly Phe Ser Phe Asp Arg Asn
            20                  25                  30

Tyr Trp Ile Ser Trp Ile Arg Gln Ala Pro Gly Lys Gly Leu Glu Trp
        35                  40                  45

Ala Ala Val Ile Ser Ala Gly Gly Ser Gly Asn Thr Tyr Tyr Ala Thr

```
            50                  55                  60
Trp Ala Lys Gly Arg Phe Thr Ile Ser Lys Asp Asn Ser Lys Asn Thr
 65                  70                  75                  80

Val Tyr Leu Gln Met Asn Ser Leu Arg Ala Glu Asp Thr Ala Val Tyr
                 85                  90                  95

Phe Cys Ala Arg Phe Tyr Ser Gly Gly Tyr Tyr Ala Gly Tyr Phe
                100                 105                 110

Thr Leu Trp Gly Gln Gly Thr Leu Val Thr Val Ser Ser
            115                 120                 125

<210> SEQ ID NO 25
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 25

Gln Val Gln Leu Val Gln Ser Gly Gly Gly Val Val Gln Pro Gly Glu
 1               5                  10                  15

Ser Leu Arg Leu Ser Cys Ala Val Ser Gly Phe Ser Phe Asp Arg Asn
                 20                  25                  30

Tyr Trp Ile Cys Trp Ile Arg Gln Ala Pro Gly Lys Gly Leu Glu Trp
             35                  40                  45

Ala Ala Cys Ile Ser Ala Gly Gly Ser Gly Asn Thr Tyr Tyr Ala Thr
 50                  55                  60

Trp Ala Lys Gly Arg Phe Thr Ile Ser Lys Asp Asn Ser Lys Asn Thr
 65                  70                  75                  80

Val Tyr Leu Gln Met Asn Ser Leu Arg Ala Glu Asp Thr Ala Val Tyr
                 85                  90                  95

Phe Cys Ala Arg Phe Tyr Ser Gly Gly Tyr Tyr Ala Gly Tyr Phe
                100                 105                 110

Thr Leu Trp Gly Gln Gly Thr Leu Val Thr Val Ser Ser
            115                 120                 125

<210> SEQ ID NO 26
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 26

Gln Xaa Gln Leu Val Gln Ser Gly Gly Gly Val Val Gln Pro Gly Glu
 1               5                  10                  15

Ser Leu Arg Leu Ser Cys Ala Val Ser Gly Phe Ser Phe Asp Arg Asn
                 20                  25                  30

Tyr Trp Ile Ala Trp Ile Arg Gln Ala Pro Gly Lys Gly Leu Glu Trp
             35                  40                  45

Ala Ala Val Ile Ser Ala Gly Gly Ser Gly Asn Thr Tyr Tyr Ala Thr
 50                  55                  60

Trp Ala Lys Gly Arg Phe Thr Ile Ser Lys Asp Asn Ser Lys Asn Thr
 65                  70                  75                  80

Val Tyr Leu Gln Met Asn Ser Leu Arg Ala Glu Asp Thr Ala Val Tyr
                 85                  90                  95
```

```
Phe Cys Ala Arg Phe Tyr Ser Gly Gly Gly Tyr Tyr Ala Gly Tyr Phe
                100                 105                 110

Thr Leu Trp Gly Gln Gly Thr Leu Val Thr Val Ser Ser
        115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (78)..(78)
<223> OTHER INFORMATION: Xaa can be any naturally occurring amino acid

<400> SEQUENCE: 27

Gln Val Gln Leu Val Gln Ser Gly Gly Gly Val Val Gln Pro Gly Glu
1               5                   10                  15

Ser Leu Arg Leu Ser Cys Ala Val Ser Gly Phe Ser Phe Asp Arg Asn
            20                  25                  30

Tyr Trp Ile Ala Trp Ile Arg Gln Ala Pro Gly Lys Gly Leu Glu Trp
        35                  40                  45

Ala Ala Val Ile Ser Ala Gly Gly Ser Gly Asn Thr Tyr Tyr Ala Thr
    50                  55                  60

Trp Ala Lys Gly Arg Phe Thr Ile Ser Lys Thr Ser Ser Xaa Thr Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
                100                 105                 110

Thr Leu Trp Gly Gln Gly Thr Leu Val Thr Val Ser Ser
        115                 120                 125

<210> SEQ ID NO 28
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 28

Gln Xaa Gln Leu Val Gln Ser Gly Gly Gly Val Val Gln Pro Gly Glu
1               5                   10                  15

Ser Leu Arg Leu Ser Cys Ala Val Ser Gly Phe Ser Phe Asp Arg Asn
            20                  25                  30

Tyr Trp Ile Ala Trp Ile Arg Gln Ala Pro Gly Lys Gly Leu Glu Trp
        35                  40                  45

Ala Ala Val Ile Ser Ala Gly Gly Ser Gly Asn Thr Tyr Tyr Ala Thr
    50                  55                  60

Trp Ala Lys Gly Arg Phe Thr Ile Ser Lys Thr Ser Ser Xaa Thr Thr
65                  70                  75                  80

Val Tyr Leu Gln Met Asn Ser Leu Arg Ala Glu Asp Thr Ala Val Tyr
```

```
                     85                  90                  95
Phe Cys Ala Arg Phe Tyr Ser Gly Gly Gly Tyr Tyr Ala Gly Tyr Phe
                100                 105                 110

Thr Leu Trp Gly Gln Gly Thr Leu Val Thr Val Ser Ser
        115                 120                 125

<210> SEQ ID NO 29
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 29

Gln Xaa Gln Leu Val Gln Ser Gly Gly Gly Val Val Gln Pro Gly Glu
1               5                   10                  15

Ser Leu Arg Leu Ser Cys Ala Val Ser Gly Phe Ser Phe Asp Arg Asn
                20                  25                  30

Tyr Trp Ile Ser Trp Ile Arg Gln Ala Pro Gly Lys Gly Leu Glu Trp
            35                  40                  45

Ala Ala Val Ile Ser Ala Gly Gly Ser Gly Asn Thr Tyr Tyr Ala Thr
        50                  55                  60

Trp Ala Lys Gly Arg Phe Thr Ile Ser Lys Thr Ser Ser Xaa Thr Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
                100                 105                 110

Thr Leu Trp Gly Gln Gly Thr Leu Val Thr Val Ser Ser
        115                 120                 125

<210> SEQ ID NO 30
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 30

Gln Xaa Gln Leu Val Gln Ser Gly Gly Gly Val Val Gln Pro Gly Glu
1               5                   10                  15

Ser Leu Arg Leu Ser Cys Ala Val Ser Gly Phe Ser Phe Asp Arg Asn
                20                  25                  30

Tyr Trp Ile Cys Trp Ile Arg Gln Ala Pro Gly Lys Gly Leu Glu Trp
            35                  40                  45

Ala Ala Cys Ile Ser Ala Gly Gly Ser Gly Asn Thr Tyr Tyr Ala Thr
        50                  55                  60
```

Trp Ala Lys Gly Arg Phe Thr Ile Ser Lys Thr Ser Ser Xaa Thr Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
            115                 120                 125

<210> SEQ ID NO 31
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 31

Gly Phe Ser Phe Asp Arg Asn Tyr Trp Ile Ala
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 32

Gly Phe Ser Phe Asp Arg Asn Tyr Trp Ile Ser
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (11)..(11)
<223> OTHER INFORMATION: Xaa can be any naturally occurring amino acid

<400> SEQUENCE: 33

Gly Phe Ser Phe Asp Arg Asn Tyr Trp Ile Xaa
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 34

Val Ile Ser Ala Gly Gly Ser Gly Asn Thr Tyr Tyr Ala Thr Trp Ala
1               5                   10                  15

Lys Gly

<210> SEQ ID NO 35
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 35

Ala Ile Ser Ala Gly Gly Ser Gly Asn Thr Tyr Tyr Ala Thr Trp Ala
1               5                   10                  15

Lys Gly

<210> SEQ ID NO 36
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 36

Gly Ile Ser Ala Gly Gly Ser Gly Asn Thr Tyr Tyr Ala Thr Trp Ala
1               5                   10                  15

Lys Gly

<210> SEQ ID NO 37
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 37

Xaa Ile Ser Ala Gly Gly Ser Gly Asn Thr Tyr Tyr Ala Thr Trp Ala
1               5                   10                  15

Lys Gly

<210> SEQ ID NO 38
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 38

Ala Phe Glu Leu Thr Gln Thr Thr Ser Pro Val Ser Ala Ala Val Gly
1               5                   10                  15

Gly Thr Val Thr Ile Phe Cys Gln Ala Ser Gln Ser Ile Gly Asn Asn
                20                  25                  30

Leu Ala Trp Tyr Gln Gln Lys Pro Gly Gln Pro Pro Lys Leu Leu Ile
            35                  40                  45

Tyr Leu Ala Ser Tyr Leu Ala Ser Gly Val Pro Ser Arg Phe Lys Gly
        50                  55                  60

Ser Gly Ser Gly Thr Gln Phe Thr Leu Thr Val Ser Ala Leu Glu Cys
65                  70                  75                  80

Ala Asp Ala Ala Ala Tyr Tyr Cys Gln Ser Ala Tyr Tyr Ser Pro Asn
                85                  90                  95

Asp Asn Ala Phe Gly Gly Gly Thr Glu Val Val Val Arg
                100                 105

<210> SEQ ID NO 39
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 39

Ala Ile Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Gly Asn Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ala Tyr Tyr Ser Pro Asn
                85                  90                  95

Asp Asn Ala Phe Gly Gln Gly Thr Lys Val Glu Ile Lys
            100                 105

<210> SEQ ID NO 40
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 40

Gln Ala Ser Gln Ser Ile Gly Asn Asn Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 41

Leu Ala Ser Tyr Leu Ala Ser
1               5

<210> SEQ ID NO 42
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 42

Gln Ser Ala Tyr Tyr Ser Pro Asn Asp Asn Ala
1               5                   10

<210> SEQ ID NO 43
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 43

Gln Xaa Ser Leu Glu Glu Ser Gly Gly Asp Leu Val Lys Pro Gly Ala
1               5                   10                  15

Ser Leu Thr Leu Thr Cys Thr Ala Ser Gly Phe Ser Phe Asp Arg Asn
            20                  25                  30

Tyr Trp Met Cys Trp Val Arg Gln Ala Pro Gly Met Gly Leu Glu Trp
        35                  40                  45

Ala Ala Cys Ile Ala Ala Gly Gly Asn Gly Asn Thr Tyr Tyr Ala Thr
50                  55                  60

Trp Ala Lys Gly Arg Phe Thr Ile Ser Lys Thr Ser Thr Xaa Thr
65                  70                  75                  80

Val Thr Leu Gln Met Ala Ser Leu Thr Ala Ala Asp Thr Ala Thr Tyr
                85                  90                  95

Phe Cys Ala Arg Phe Tyr Asn Gly Gly Gly Tyr Tyr Ala Gly Tyr Phe
            100                 105                 110

Thr Leu Trp Gly Pro Gly Thr Leu Val Thr Val Ser Ser
            115                 120                 125

<210> SEQ ID NO 44
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (101)..(114)
<223> OTHER INFORMATION: Xaa can be any naturally occurring amino acid

<400> SEQUENCE: 44

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Xaa
            20                  25                  30

Tyr Ala Met His Trp Val Arg Gln Ala Pro Gly Lys Gly Leu Glu Trp
        35                  40                  45

Val Ala Val Ile Ser Tyr Asp Xaa Gly Ser Asn Lys Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Xaa Xaa Xaa Xaa Xaa Xaa Xaa Xaa Xaa Xaa Xaa
            100                 105                 110

Xaa Xaa Trp Gly Gln Gly Thr Leu Val Thr Val Ser Ser
            115                 120                 125

<210> SEQ ID NO 45
<211> LENGTH: 11
<212> TYPE: PRT
<213> ORGANISM: Artificial Sequence
<220> FEATURE:
<223> OTHER INFORMATION: Synthetic Polypeptide

```
<400> SEQUENCE: 45

Gly Phe Ser Phe Asp Arg Asn Tyr Trp Met Cys
1               5                  10

<210> SEQ ID NO 46
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 46

Cys Ile Ala Ala Gly Gly Asn Gly Asn Thr Tyr Tyr Ala Thr Trp Ala
1               5                  10                  15

Lys Gly

<210> SEQ ID NO 47
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 47

Phe Tyr Asn Gly Gly Gly Tyr Tyr Ala Gly Tyr Phe Thr Leu
1               5                  10

<210> SEQ ID NO 48
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 48

Ala Ile Gln Leu Thr Gln Ser Pro Ser Ser Leu Ser Ala Ser Val Gly
1               5                  10                  15

Asp Arg Val Thr Ile Thr Cys Gln Ala Ser Gln Ser Ile Gly Asn Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ala Tyr Tyr Ser Pro Asn
                85                  90                  95

Asp Asn Ala Phe Gly Gln Gly Thr Lys Val Glu Ile Lys
            100                 105

<210> SEQ ID NO 49
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 49

Ala Phe Gln Leu Thr Gln Ser Pro Ser Ser Leu Ser Ala Ser Val Gly
1               5                  10                  15

Asp Arg Val Thr Ile Thr Cys Gln Ala Ser Gln Ser Ile Gly Asn Asn
```

```
            20                  25                  30
Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ala Tyr Tyr Ser Pro Asn
                85                  90                  95

Asp Asn Ala Phe Gly Gln Gly Thr Lys Val Glu Ile Lys
            100                 105

<210> SEQ ID NO 50
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 50

Ala Phe Gln Leu Thr Gln Ser Pro Ser Ser Leu Ser Ala Ser Val Gly
1               5                   10                  15

Asp Arg Val Thr Ile Phe Cys Gln Ala Ser Gln Ser Ile Gly Asn Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Gln Phe Thr Leu Thr Val Ser Ser Leu Gln Pro
65                  70                  75                  80

Glu Asp Phe Ala Thr Tyr Tyr Cys Gln Ser Ala Tyr Tyr Ser Pro Asn
                85                  90                  95

Asp Asn Ala Phe Gly Gln Gly Thr Lys Val Glu Ile Lys
            100                 105

<210> SEQ ID NO 51
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Asp Arg Asn
            20                  25                  30

Tyr Trp Met Ala Trp Val Arg Gln Ala Pro Gly Lys Gly Leu Glu Trp
        35                  40                  45

Val Ala Val Ile Ala Ala Gly Gly Ser Gly Asn Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Phe Tyr Ser Gly Gly Gly Tyr Tyr Ala Gly Tyr Phe
            100                 105                 110
```

```
Thr Leu Trp Gly Gln Gly Thr Leu Val Thr Val Ser Ser
        115                 120                 125
```

<210> SEQ ID NO 52
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 52

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ser Phe Asp Arg Asn
            20                  25                  30

Tyr Trp Met Ala Trp Val Arg Gln Ala Pro Gly Lys Gly Leu Glu Trp
        35                  40                  45

Val Ala Val Ile Ala Ala Gly Gly Ser Gly Asn Thr Tyr Tyr Ala Thr
    50                  55                  60

Trp Ala Lys Gly Arg Phe Thr Ile Ser Lys Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
        115                 120                 125
```

<210> SEQ ID NO 53
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 53

```
Gln Val Gln Leu Val Gln Ser Gly Gly Gly Val Val Gln Pro Gly Glu
1               5                   10                  15

Ser Leu Arg Leu Ser Cys Ala Ala Ser Gly Phe Ser Phe Asp Arg Asn
            20                  25                  30

Tyr Trp Met Ala Trp Val Arg Gln Ala Pro Gly Lys Gly Leu Glu Trp
        35                  40                  45

Ala Ala Val Ile Ala Ala Gly Gly Ser Gly Asn Thr Tyr Tyr Ala Thr
    50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
        115                 120                 125
```

<210> SEQ ID NO 54
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 54

```
Gln Val Gln Leu Val Gln Ser Gly Gly Gly Val Val Gln Pro Gly Glu
1               5                   10                  15

Ser Leu Arg Leu Ser Cys Ala Ala Ser Gly Phe Ser Phe Asp Arg Asn
            20                  25                  30

Tyr Trp Met Ser Trp Val Arg Gln Ala Pro Gly Lys Gly Leu Glu Trp
        35                  40                  45

Ala Ala Val Ile Ala Ala Gly Gly Ser Gly Asn Thr Tyr Tyr Ala Thr
    50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
        115                 120                 125
```

<210> SEQ ID NO 55
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 55

```
Gln Val Gln Leu Val Gln Ser Gly Gly Gly Val Val Gln Pro Gly Glu
1               5                   10                  15

Ser Leu Arg Leu Ser Cys Ala Ala Ser Gly Phe Ser Phe Asp Arg Asn
            20                  25                  30

Tyr Trp Met Cys Trp Val Arg Gln Ala Pro Gly Lys Gly Leu Glu Trp
        35                  40                  45

Ala Ala Cys Ile Ala Ala Gly Gly Ser Gly Asn Thr Tyr Tyr Ala Thr
    50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
        115                 120                 125
```

<210> SEQ ID NO 56
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 56

```
Gln Xaa Gln Leu Val Gln Ser Gly Gly Gly Val Val Gln Pro Gly Glu
1               5                   10                  15

Ser Leu Arg Leu Ser Cys Ala Ala Ser Gly Phe Ser Phe Asp Arg Asn
            20                  25                  30
```

```
Tyr Trp Met Ala Trp Val Arg Gln Ala Pro Gly Lys Gly Leu Glu Trp
            35                  40                  45

Ala Ala Val Ile Ala Ala Gly Gly Ser Gly Asn Thr Tyr Tyr Ala Thr
        50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
            115                 120                 125

<210> SEQ ID NO 57
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (78)..(78)
<223> OTHER INFORMATION: Xaa can be any naturally occurring amino acid

<400> SEQUENCE: 57

Gln Val Gln Leu Val Gln Ser Gly Gly Gly Val Val Gln Pro Gly Glu
1               5                   10                  15

Ser Leu Arg Leu Ser Cys Ala Ala Ser Gly Phe Ser Phe Asp Arg Asn
            20                  25                  30

Tyr Trp Met Ala Trp Val Arg Gln Ala Pro Gly Lys Gly Leu Glu Trp
            35                  40                  45

Ala Ala Val Ile Ala Ala Gly Gly Ser Gly Asn Thr Tyr Tyr Ala Thr
        50                  55                  60

Trp Ala Lys Gly Arg Phe Thr Ile Ser Lys Thr Ser Ser Xaa Thr Thr
65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
            115                 120                 125

<210> SEQ ID NO 58
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 58

Gln Xaa Gln Leu Val Gln Ser Gly Gly Gly Val Val Gln Pro Gly Glu
1               5                   10                  15

Ser Leu Arg Leu Ser Cys Ala Ala Ser Gly Phe Ser Phe Asp Arg Asn
```

```
            20                  25                  30
Tyr Trp Met Ala Trp Val Arg Gln Ala Pro Gly Lys Gly Leu Glu Trp
            35                  40                  45

Ala Ala Val Ile Ala Ala Gly Gly Ser Gly Asn Thr Tyr Tyr Ala Thr
        50                  55                  60

Trp Ala Lys Gly Arg Phe Thr Ile Ser Lys Thr Ser Ser Xaa Thr Thr
 65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
            115                 120                 125

<210> SEQ ID NO 59
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 59

Gln Xaa Gln Leu Val Gln Ser Gly Gly Gly Val Val Gln Pro Gly Glu
 1               5                  10                  15

Ser Leu Arg Leu Ser Cys Ala Ala Ser Gly Phe Ser Phe Asp Arg Asn
            20                  25                  30

Tyr Trp Met Ser Trp Val Arg Gln Ala Pro Gly Lys Gly Leu Glu Trp
            35                  40                  45

Ala Ala Val Ile Ala Ala Gly Gly Ser Gly Asn Thr Tyr Tyr Ala Thr
        50                  55                  60

Trp Ala Lys Gly Arg Phe Thr Ile Ser Lys Thr Ser Ser Xaa Thr Thr
 65                  70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
            115                 120                 125

<210> SEQ ID NO 60
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 60
```

Gln Xaa Gln Leu Val Gln Ser Gly Gly Gly Val Val Gln Pro Gly Glu
1               5                   10                  15

Ser Leu Arg Leu Ser Cys Ala Ala Ser Gly Phe Ser Phe Asp Arg Asn
            20                  25                  30

Tyr Trp Met Cys Trp Val Arg Gln Ala Pro Gly Lys Gly Leu Glu Trp
        35                  40                  45

Ala Ala Cys Ile Ala Ala Gly Gly Ser Gly Asn Thr Tyr Tyr Ala Thr
    50                  55                  60

Trp Ala Lys Gly Arg Phe Thr Ile Ser Lys Thr Ser Xaa Thr Thr
65              70                  75                  80

Val Tyr Leu Gln Met Asn Ser Leu Arg Ala Glu Asp Thr Ala Val Tyr
                85                  90                  95

Phe Cys Ala Arg Phe Tyr Ser Gly Gly Gly Tyr Tyr Ala Gly Tyr Phe
            100                 105                 110

Thr Leu Trp Gly Gln Gly Thr Leu Val Thr Val Ser Ser
        115                 120                 125

<210> SEQ ID NO 61
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 61

Gly Phe Ser Phe Asp Arg Asn Tyr Trp Met Ala
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 62

Gly Phe Ser Phe Asp Arg Asn Tyr Trp Met Ser
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (11)..(11)
<223> OTHER INFORMATION: Xaa can be any naturally occurring amino acid

<400> SEQUENCE: 63

Gly Phe Ser Phe Asp Arg Asn Tyr Trp Met Xaa
1               5                   10

<210> SEQ ID NO 64
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 64

Val Ile Ala Ala Gly Gly Ser Gly Asn Thr Tyr Tyr Ala Thr Trp Ala

```
<210> SEQ ID NO 65
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 65

Xaa Ile Ala Ala Gly Gly Ser Gly Asn Thr Tyr Tyr Ala Thr Trp Ala
1               5                   10                  15

Lys Gly

<210> SEQ ID NO 66
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 66

Ala Phe Gln Leu Thr Gln Ser Pro Ser Ser Leu Ser Ala Ser Val Gly
1               5                   10                  15

Asp Arg Val Thr Ile Asn Cys Gln Ala Ser Gln Ser Ile Gly Gly Asn
            20                  25                  30

Leu Ala Trp Tyr Gln Gln Lys Pro Gly Lys Ala Pro Lys Leu Leu Ile
        35                  40                  45

Tyr Leu Ala Ser Tyr Leu Ala Ser Gly Val Pro Ser Arg Phe Ser Gly
    50                  55                  60

Ser Gly Ser Gly Thr Gln Phe Thr Leu Thr Val Ser Ser Leu Gln Pro
65                  70                  75                  80

Glu Asp Phe Ala Thr Tyr Tyr Cys Gln Ser Ser Tyr Tyr Ser Pro Asn
                85                  90                  95

Asp Asn Ala Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 67
<211> LENGTH: 454
<212> TYPE: PRT
```

<213> ORGANISM: Artificial Sequence
<220> FEATURE:
<223> OTHER INFORMATION: Synthetic Polypeptide

<400> SEQUENCE: 67

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Asp Arg Asn
            20                  25                  30

Tyr Trp Ile Ala Trp Val Arg Gln Ala Pro Gly Lys Gly Leu Glu Trp
        35                  40                  45

Val Ala Ala Ile Ser Ala Gly Gly Ser Gly Asn Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Phe Tyr Ser Gly Gly Tyr Tyr Ala Gly Tyr Phe
            100                 105                 110

Thr Leu Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
```

```
                385                 390                 395                 400
Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly
        450

<210> SEQ ID NO 68
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 68

Met Arg Val Pro Ala Gln Leu Leu Gly Leu Leu Leu Leu Trp Leu Pro
1               5                   10                  15

Gly Ala Arg Cys
            20

<210> SEQ ID NO 69
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 69

Met Asp Phe Gly Leu Ser Trp Val Phe Leu Val Leu Val Leu Lys Gly
1               5                   10                  15

Val Gln Cys

<210> SEQ ID NO 70
<211> LENGTH: 1422
<212> TYPE: DNA
<213> ORGANISM: Artificial Sequence
<220> FEATURE:
<223> OTHER INFORMATION: Synthetic Polynucleotide

<400> SEQUENCE: 70
atggacttcg gcctgtcctg ggtgttcctg gtgctggtgc tgaagggcgt gcagtgccag      60
gtgcagctgg tggaatccgg cggtggcgtg gtgcagcctg gcagatccct gagactgtcc     120
tgcgccgcct ccggcttctc cttcgaccgg aactactgga tcgcctgggt ccgacaggcc     180
cctggcaagg gactggaatg ggtggccgcc atctccgctg gcggctccgg caacacctac     240
tacgccacct gggccaaggg ccggttcacc atctcccggg acaactccaa gaacaccctg     300
tacctgcaga tgaactccct gcgggccgag gacaccgccg tgtactactg cgcccggttc     360
tacagcggcg gaggctacta cgccggctac ttcaccctgt ggggccaggg caccctggtc     420
accgtgtcct ccgcctctac caagggcccc tccgtgttcc ctctggcccc ctccagcaag     480
tccacctctg gcggcaccgc cgctctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc cagcagcttg     660
ggcacccaga cctacatctg caacgtgaat cacaagccca gcaacaccaa ggtggacaag     720
```

-continued

```
aaagttgagc ccaaatcttg tgacaagact cacacatgcc caccgtgccc agcacctgaa      780
ctcctggggg gaccgtcagt cttcctcttc cccccaaaac ccaaggacac cctcatgatc      840
tcccggaccc ctgaggtcac atgcgtggtg gtggacgtga gccacgaaga ccctgaggtc      900
aagttcaact ggtacgtgga cggcgtggag gtgcataatg ccaagacaaa gccgcgggag      960
gagcagtaca acagcacgta ccgtgtggtc agcgtcctca ccgtcctgca ccaggactgg     1020
ctgaatggca aggagtacaa gtgcaaggtc tccaacaaag ccctcccagc ccccatcgag     1080
aaaaccatct ccaaagccaa agggcagccc cgagaaccac aggtgtacac cctgccccca     1140
tcccgggatg agctgaccaa gaaccaggtc agcctgacct gcctggtcaa aggcttctat     1200
cccagcgaca tcgccgtgga gtgggagagc aatgggcagc cggagaacaa ctacaagacc     1260
acgcctcccg tgttggactc cgacggctcc ttcttcctct acagcaagct caccgtggac     1320
aagagcaggt ggcagcaggg gaacgtcttc tcatgctccg tgatgcatga ggctctgcac     1380
aaccactaca cgcagaagag cctctccctg tctccggtt ga                         1422
```

<210> SEQ ID NO 71
<211> LENGTH: 711
<212> TYPE: DNA
<213> ORGANISM: Artificial Sequence
<220> FEATURE:
<223> OTHER INFORMATION: Synthetic Polynucleotide

<400> SEQUENCE: 71

```
atgagggtcc ccgctcagct cctggggctc cttctgctct ggctccctgg agccagatgt       60
gccttccagc tgacccagtc ccccagctcc ctgtctgcct ccgtgggcga cagagtgacc      120
atcaactgtc aggcctccca gtccatcggc ggcaacctgg cctggtatca gcagaagccc      180
ggcaaggccc ccaagctgct gatctacctg gcctcctacc tggccagcgg cgtgccctcc      240
agattctccg gctctggctc cggcacccag tttaccctga ccgtgtccag cctgcagccc      300
gaggacttcg ccacctacta ctgccagtcc tctactact ccccccaacga caacgccttc      360 ggccagggca ccaaggtgga aatcaagcgt acggtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgtta g              711
```